(12) United States Patent
Carlson et al.

(10) Patent No.: US 9,376,385 B2
(45) Date of Patent: Jun. 28, 2016

(54) SOLID-PHASE SUPPORTS AND USES THEREOF

(71) Applicant: Indiana University Research and Technology Corporation, Indianpolis, IN (US)

(72) Inventors: Erin C. Carlson, Minneapolis, MN (US); Darci Trader, Jupiter, FL (US); Ashley Sidebottom, Saint Louis Park, MN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 14/630,183

(22) Filed: Feb. 24, 2015

(65) Prior Publication Data

US 2015/0240006 A1 Aug. 27, 2015

Related U.S. Application Data

(60) Provisional application No. 61/944,235, filed on Feb. 25, 2014.

(51) Int. Cl.
| | |
|---|---|
| *C07F 7/04* | (2006.01) |
| *C07D 207/36* | (2006.01) |
| *C07D 273/00* | (2006.01) |
| *C07D 273/01* | (2006.01) |
| *C08F 8/30* | (2006.01) |
| *C08F 8/42* | (2006.01) |

(52) U.S. Cl.
CPC ............ *C07D 207/36* (2013.01); *C07D 273/00* (2013.01); *C07D 273/01* (2013.01); *C08F 8/30* (2013.01); *C08F 8/42* (2013.01)

(58) Field of Classification Search
CPC ....... C08F 112/08; C08F 8/30; C07D 273/01; C07D 207/36; A01N 43/56
USPC ......................................................... 556/431
See application file for complete search history.

(56) References Cited

U.S. PATENT DOCUMENTS 4,721,800 A 1/1988 Chapman

OTHER PUBLICATIONS

Trader et al., Organic Letters (2011), 13(20), 5652-5655.*
Newman, David J., and Gordon M. Cragg. "Natural Products as Sources of New Drugs over the Last 25 Years." Journal of natural products 70.3 (2007): 461-477.
Carlson, Erin E. "Natural products as chemical probes." ACS chemical biology 5.7 (2010): 639-653.
Böttcher, Thomas, Maximilian Pitscheider, and Stephan A. Sieber. "Natural products and their biological targets: proteomic and metabolomic labeling strategies." Angewandte Chemie International Edition 49.15 (2010): 2680-2698.
Månsson, Maria, et al. "Explorative solid-phase extraction (E-SPE) for accelerated microbial natural product discovery, dereplication, and purification." Journal of Natural Products 73.6 (2010): 1126-1132.
Araya, Juan J., et al. "Application of phase-trafficking methods to natural products research." Journal of natural products 73.9 (2010): 1568-1572.
Watve, Milind G., et al. "How many antibiotics are produced by the genus Streptomyces?." Archives of microbiology 176.5 (2001): 386-390.
Carlson, Erin E., and Benjamin F. Cravatt. "Chemoselective probes for metabolite enrichment and profiling." Nature methods 4.5 (2007): 429-435.
Carlson, Erin E., and Benjamin F. Cravatt. "Enrichment tags for enhanced-resolution profiling of the polar metabolome." Journal of the American Chemical Society 129.51 (2007): 15780-15782.
Odendaal, Antoinette Y., Darci J. Trader, and Erin E. Carlson. "Chemoselective enrichment for natural products discovery." Chemical Science 2.4 (2011): 760-764.
Henkel, Thomas, et al. "Statistical investigation into the structural complementarity of natural products and synthetic compounds." Angewandte Chemie International Edition 38.5 (1999): 643-647.
Bringmann, G.; Reichert, Y.; Kane, V. V., "The total synthesis of streptonigrin and related antitumor antibiotic natural products", *Tetrahedron* 2004, 60, 3539.
Meloni, Marco M., et al. "Synthesis and applications of tert-alkoxysilane linkers in solid-phase chemistry." Tetrahedron 63.2 (2007): 299-311.
Weinberg, Jennifer M., Stephen P. Gitto, and Karen L. Wooley. "Synthesis and Characterization of Degradable Poly (silyl ester) s." Macromolecules 31.1 (1998): 15-21.
Wang, Min, Jennifer M. Weinberg, and Karen L. Wooley. "Synthesis, Characterization and Degradation of Poly (silyl ester) s." Macromolecules 31.22 (1998): 7606-7612.
Ojima, Yuko, Kazuya Yamaguchi, and Noritaka Mizuno. "An Efficient Solvent-Free Route to Silyl Esters and Silyl Ethers." Advanced Synthesis & Catalysis 351.9 (2009): 1405-1411.
Liang, Huan, Lin Hu, and E. J. Corey. "Di-tert-butylisobutylsilyl, Another Useful Protecting Group." Organic Letters 13.15 (2011): 4120-4123.
Huczynski, A.; Stefanska, J.; Przybylski, P.; Brzezinski, B.; Bartl, F., "Synthesis and antimicrobial properties of Monensin A esters",Bioorg. Med. Chem. Lett. 2008, 18, 2585.
Wallace, K. K.; Payne, G. F.; Speedie, M. K., Ammonium effects on streptonigrin biosynthesis by *Streptomyces, J. Ind. Microbiol. Biotechnol.* 1990, 6, 43.

(Continued)

*Primary Examiner* — Porfirio Nazario Gonzalez
*Assistant Examiner* — Kofi Adzamli
(74) *Attorney, Agent, or Firm* — Barnes & Thornburg LLP

(57) ABSTRACT

The present disclosure relates to solid-phase azide supports, methods for making solid-state azide supports, and methods for capturing alkynes using the same. The present disclosure also relates to kits for solid-phase azide supports.

17 Claims, 5 Drawing Sheets

(56) References Cited

OTHER PUBLICATIONS

Mbah, Godfrey C., and John L. Speier. " Equilibria between MexSiCl4-x, x = 3, 2, 1, 0 and alkyl carboxylate esters." Journal of organometallic chemistry 271.1 (1984): 77-82.

Chauhan, Moni, Bhanu PS Chauhan, and Philip Boudjouk. "An efficient Pd-catalyzed route to silyl esters." Organic letters 2.8 (2000): 1027-1029.

Huang, Xiaogen, et al. "Silyl methallylsulfinates: efficient and powerful agents for the chemoselective silylation of alcohols, polyols, phenols and carboxylic acids." Chemical communications 10 (2005): 1297-1299.

Clardy, Jon, and Christopher Walsh. "Lessons from natural molecules." Nature 432.7019 (2004): 829-837.

Newman, D. J.; "Natural Products as Sources of New Drugs over the 30 Years from 1981 to 2010", Cragg, G. M. *J. Nat. Prod.* 2012, 75, 311.

Koehn, Frank E., and Guy T. Carter. "The Evolving Role of Natural Products in Drug Discovery." Nature Reviews Drug Discovery 4.3 (2005): 206-220.

Butler, Mark S. "The role of natural product chemistry in drug discovery." Journal of Natural Products 67.12 (2004): 2141-2153.

Sticher, Otto. "Natural product isolation." Natural product reports 25.3 (2008): 517-554.

Gualtieri, Maxime, et al. "The Antibiotics in the Chemical Space." Current Medicinal Chemistry 16.3 (2009): 390-393.

Hu, Yonghan, et al. "Novel polymer-supported trialkylsilanes and their use in solid-phase organic synthesis." The Journal of Organic Chemistry 63.13 (1998): 4518-4521.

DiBlasi, Christine M., Daniel E. Macks, and Derek S. Tan. "An acid-stable tert-butyldiarylsilyl (TBDAS) linker for solid-phase organic synthesis." Organic letters 7.9 (2005): 1777-1780.

Cheminat, Annie, et al. "Removal of allergens from natural oils by selective binding to polymer supports. II. Application of aminated resins to isoalantolactone and costus oil." *Canadian Journal of Chemistry* 59.10 (1981): 1405-1414.

Boehm, Terri L., and HD Hollis Showalter. "Development of a Novel Silyl Ether Linker for Solid-Phase Organic Synthesis." The Journal of organic chemistry 61.19 (1996): 6498-6499.

B. A. Sobin and J. Tanner, F. W., "Anisomycin, a New Anti-protozoan Antibiotic", J. Am. Chem. Soc., 1954, 76, 4053.

J. M. J. Frechet, A. J. Hagen, C. Benezra, & A. Cheminat, "Polymeric Separation Media: Binding alpha,.beta.-Unsaturated Carbonyl Compounds to Insoluble Resins through Michael Additions or Chelation of Derivatives," Pure & Appl. Chem., vol. 54, No. 11 (1982), pp. 2181-2188.

A. P. Grollman, "Inhibitators of Protein Biosynthesis", J. Biol. Chem., 1967, 242, 3226-3233.

Berdy, J. "Bioactive Microbial Metabolites, A Personal View", *J. Antibiot.* 2005, 58, 1.

Grabowski, Kristina, Karl-Heinz Baringhaus, and Gisbert Schneider. "Scaffold diversity of natural products: inspiration for combinatorial library design." Natural product reports 25.5 (2008): 892-904.

Tallarico, John A., et al. "An alkylsilyl-tethered, high-capacity solid support amenable to diversity-oriented synthesis for one-bead, one-stock solution chemical genetics." Journal of combinatorial chemistry 3.3 (2001): 312-318.

Trader, D. J.; Carlson, E. E. "Siloxyl Ether Functionalized Resins for Chemoselective Enrichment of Carboxylic Acids", *Org. Lett.* 2011, 13, 5652.

Trader, D. J.; Carlson, E. E. "Chemoselective hydroxyl group transformation: an elusive target" *Mol. Biosyst.* 2012, 8, 2484.

Rishton, G. M., "Natural Products as a Robust Source of New Drugs and Drug Leads: Past Successes and Present Day Issues", *Am J Cardiol* 2008, 101, 43.

Dimitrios, B., "Sources of natural phenolic antioxidants", *Trends Food Sci. Technol.* 2006, 17, 505.

Crouch, R. D., "Selective monodeprotection of bis-silyl ethers", *Tetrahedron* 2004, 60, 5833.

Crouch, R. D., "Selective deprotection of silyl ethers", *Tetrahedron* 2013, 69, 2383.

Crouch, R. D.; Stieff, M.; Frie, J. L.; Cadwallader, A. B.; Bevis, D. C., Selective Deprotection of Silyl-Protected Phenols Using Solid NaOH and a Phase Transfer Catalyst Tetrahedron Lett. 1999, 40, 3133.

Oyama, K.; Kondo, T., "A Novel and Convenient Chemoselective Deprotection Method for Both Silyl and Acetyl Groups on Acidic Hydroxyl Groups Such as Phenol and Carboxylic Acid by Using a Nitrogen Organic Base, 1,1,3,3-Tetramethylguanidine", *Org. Lett.* 2003, 5, 209.

Wilson, N. S.; Keay., B. A., "Mild Base Mediated Desilylation of Various Phenolic Silyl Ethers", *Tetrahedron Lett.* 1997, 38, 187.

Yan, L.; Zhao, F.; Gan, Y.; Zhao, J.; Jiang, Z., Chemoselective Deprotection of Aryl tert-Butyldimethylsilyl Ethers Promoted by Phosphates *Syn. Comm.* 2012, 42, 285.

Wang, B.; Sun, H.-X.; Sun, Z.-H., "LiOAc-Catalyzed Chemoselective Deprotection of Aryl Silyl Ethers under Mild Conditions", *J. Org. Chem.* 2009, 74, 1781.

Yeom, C.-E.; Kim, H. W.; Lee, S. Y.; Kim, B. M., "DBU-Mediated Mild and Chemoselective Deprotection of Aryl Silyl Ethers and Tandem Biaryl Ether Formation", *Synlett* 2007, 1, 146.

Collington, E. W.; Finch, H.; Smit, I. J., "Selective Deprotection of Alcoholic and Phenolic Silyl Ethers", *Tetrahedron Lett.* 1985, 26, 681.

Frie, J. L.; Jeffrey, C. S.; Sorenson, E. J., A Hypervalent Iodine-Induced Double Annulation Enables a Concise Synthesis of the Pentacyclic Core Structure of the Cortistatins *Org. Lett.* 2009, 11, 5394.

Karavalakis, G.; Anastopoulos, G.; Stournas, S., Tetramethylguanidine as an efficient catalyst for transesterification of waste frying oils *Appl. Energ.* 2011, 88, 3645.

Simoni, D.; Invidiata, F. P.; Manferdini, M.; Lampronti, I.; Rondanin, R.; Roberti, M.; Pollini, G. P., Tetramethylguanidine (TMG)-Catalyzed Addition of Dialkyl Phosphites to alpha, beta-Unsaturated Carbonyl Compounds, Alkenenitriles, Aldehydes, Ketones and Imines *Tetrahedron Lett.* 1998, 39, 7615.

Zhu, A.; Jiang, T.; Wang, D.; Han, B.; Liu, L.; Huang, J.; Zhang, J.; Sun, D. Direct aldol reactions catalyzed by 1,1,3,3-tetramethylguanidine lactate without solvent *Green Chem.* 2005, 7, 514.

Kovacevic, B.; Z.B., M., Basicity of Some Organic Superbases in Acetonitrile *Org. Lett.* 2001, 3, 1523.

Charest, M. G.; Siegel, D. R.; Myers, A. G., "Synthesis of (−)-Tetracycline", *J. Am. Chem. Soc.* 2005, 127, 8292.

Evans, D. A.; Dinsmore, C. J.; Ratz, A. M.; Evrard, D. A.; Barrow, J. C., Synthesis and Conformational Properties of the M(4-6)(5-7) Bicyclic Tetrapeptide Common to the Vancomycin Antibiotics *J. Am. Chem. Soc.* 1997, 119, 3417.

Yu, X. M.; Shen, G.; Necker, L.; Blake, H.; Holzbeierlein, J.; Cronk, B.; Blagg, B. S. J., "Hsp90 Inhibitors Identified from a Library of Novobiocin Analogues", *J. Am. Chem. Soc.* 2005, 127, 12778.

Wang, H.; Yeo, S. L.; Xu, J.; Xu, X.; He, H.; Ronca, F.; Ting, A. E.; Wang, Y.; Yu, V. C.; Sim, M. M., Isolation of Streptonigrin and Its Novel Derivative from Micromonospora as Inducing Agents of p53-Dependent Cell Apoptosis *J. Nat. Prod.* 2002, 65, 721.

Drahl, C.; Cravatt, B. F.; Sorenson, E. J., Protein-reactive natural products. *Angew. Chem. Int. Ed.* 2005, 44, 5788-5809.

Kluge, A. F.; Petter, R. C., Acylating drugs: redesigning natural product covalent inhibitors. *Curr. Opin. Chem. Biol* 2010, 14, 421-427.

Gersch, M.; Kreuzer, J.; Sieber, S. A., Electrophilic natural products and their bilogical targets. *Nat. Prod. Rep.* 2012, 29, 659-682.

Hubel, K.; LeBmann, T.; Waldmann, H., Chemical biology-identification of small molecules modulators of cellular activity by natural product inspired synthesis. *Chem. Soc. Rev.* 2008, 37, 1361-1374.

Krysiak, J.; Breinbauer, R., Activity-based protein profiling for natural product target discovery. *Top. Curr. Chem* 2012, 324, 43-84.

Sakamoto, S.; Hatakeyama, M.; Ito, T.; Handa, H., Tools and methodologies capable of isolating and identifying a target molecule for a bioactive compound. *Bioorg. Med. Chem.* 2012, 20, 1990-2001.

Wakimoto, T.; Abe, I., Labile natural products. *Med. Chem. Commun.* 2012, 3, 866-870.

(56) References Cited

OTHER PUBLICATIONS

Futamura, Y.; Muroi, M.; Osada, H., Target identification of small molecules based on chemical biology approaches. *Mol. Biosyst.* 2013, 9, 897-914.

Minto, R. E.; Blacklock, B. J., Biosynthesis and function of polyacetylenes and allied natural products. *Porg. Lipid Res.* 2008, 47, 233-306.

Hoffman-Roder, A.; Krause, N., Synthesis and properties of allenic natural products and pharmaceuticals. *Angew. Chem. Int. Ed.* 2004, 43, 1196-1216.

Milne, S. B.; Tallman, K. A.; Serwa, R.; Rouzer, C. A.; Armstrong, M. D.; Marnett, L. J.; Lukehart, C. M.; Porter, N. A.; Brown, H. A., Capture and release of alkyne-derivatized glycerophospholipids using cobalt chemistry. *Nat. Chem. Biol* 2012, 6, 205-207.

Comely, A. C.; Gibson, S. E.; Hales, N. J., Polymer supported cobalt carbonyl complexes as novel traceless alkyne linkers for solid-phase synthesis. *Chem. Commun.* 1999, 2075-2076.

Comley, A. C.; Gibson, S. E.; Hales, N. J.; Johnstone, C.; Stevenazzi, A., The application of polymer-bound carbonylcobalt(0) species in linker chemistry and catalysis. *Org. Biomol. Chem.* 2003, 1, 1959-1968.

Agnew, H. D.; Rhode, R. D.; Millward, S. W.; Nag, A.; Yeo, W. S.; Hein, J. E.; Pitram, S. M.; Tariq, A. A.; Burns, V. M.; Krom, R. J.; Fokin, V. V.; Sharpless, K. B.; Heath, J. R., Iterative in situ click chemistry creates antibody-like protein capture agents. *Angew. Chem. Int. Ed.* 2009, 48, 4944-4948.

Best, M. D., Click chemistry and bioorthogonal reactions: unprecedented selectivity in the labeling of biological molecules. *Biochemistry* 2009, 48, 6571-6584.

Aragao-Leoneti, V.; Campo, V. L.; Gomes, A. S.; Field, R. A.; Carvalho, I., Application of copper(I)-catalysed azide/alkyne cycloadditiona (CuAAC) 'click chemistry' in carbohydrate drug and neoglycopolymer synthesis. *Tetrahedron* 2010, 66, 9475-9492.

Srinivasan, R.; Li, J.; Ng, S. L.; Kalesh, K. A.; Yao, S. Q., Methods of using click chemistr in the discovery of enzyme inhibitors. *Nat. Protoc.* 2007, 2, 2655-2664.

Qin, G.; Santos, C.; Zhang, W.; Li, Y. M.; Kumar, A.; Erasquin, U. J.; Liu, K.; Muradov, P.; Trautner, B. W.; Cai, C., Biofunctionalization on alkylated silicon substrate surfaces via "click" chemistry. *J. Am. Chem. Soc.* 2012, 132, 16432-16441.

Ghosh, K. K.; Ha, H. H.; Kang, N. Y.; Chandran, Y.; Chang, Y. T., Solid phase combinatorial synthesis of a xanthone library using click chemistry and its application to an embryonic stem cell probe. *Chem. Commun.* 2011, 47, 7488-7490.

Jølck, R. I.; Berg, R. H.; Andresen, T. L., Solid-Phase synthesos of PEGylated lipopeptides using click chemistry. *Bioconjugate Chem.* 2012, 21, 807-810.

Löber, S.; Gmeiner, P., Click chemisstry on solid support: synthesis of a new REM resin and application for the preparation of tertiary amines. *Tetrahedron* 2004, 60, 8699-8702.

Ardes-Guisot, N.; Alonzi, D. S.; Reinkensmeier, G.; Butters, T. D.; Norez, C.; Becq, F.; Shimada, Y.; Nakagawa, S.; Kato, A.; Bieriot, Y.; Sollogoub, M.; Vauzeilles, B., Selection of the biological activity of DNJ neoglycoconjugates through click length variation of the side chain. *Org. Biomol. Chem.* 2011, 9, 5373-5388.

Wu, P.; Feldman, A. K.; Nugent, A. K.; Hawker, C. J.; Scheel, A.; Voit, B.; Pyun, J.; Fréchet, J. M. J.; Sharpless, K. B.; Fokin, V. V., Efficiency and fidelity in a click-chemistry route to triazole dendrimers by the copper(I)-catalyzed ligation of azides and alkynes. *Angew. Chem. Int. Ed.* 2004, 43, 3928-3932.

Hein, J. E.; Fokin, V. V., Copper-catalyzed azide-alkyne cycloaddition (CuAAC) and beyond: new reactivity of copper (I) acetylides. *Chem. Soc. Rev.* 2010, 39, 1302-1315.

Helms, B. A.; Mynar, J. L.; Hawker, C. J.; Fréchet, J. M. J., Dendronized linear polymers via "click chemistry". *J. Am. Chem. Soc.* 2004, 126, 15020-15021.

Edwards, D. J.; Marquez, B. L.; Nogle, L. M.; McPhail, K.; Goeger, D. E.; Roberts, M. A.; Gerwick, W. H., Structure and biosynthesis of the jamaicamides, new mixed polyketide-peptide neurotoxins from the marine cyanobacterium lyngbya majuscula. *Chem. Biol.* 2004, 11, 817-833.

Boren, B. C.; Narayan, S.; Rasmussen, L. K.; Zhang, L.; Zhao, H. Y.; Lin, Z.; Jia, G.; Fokin, V. V., Ruthenium-catalyzed azide-alkyne cycloaddition: scope and mechanism., Tingting Mo, Wipf Group Current Literature, Jun. 28, 2008.

Zhang, L.; Chen, X.; Xue, P.; Sun, H. H. Y.; Williams, I. D.; Sharpless, K. B.; Fokin, V. V.; Jia, G., Ruthenium-catalyzed cycloaddition of alkynes and organic azides. *J. Am. Chem. Soc.* 2005, 127, 15998-15999.

\* cited by examiner

SOLID-PHASE SUPPORTS AND USES THEREOF

CROSS-REFERENCE TO RELATED APPLICATIONS

This application claims the benefit under 35 U.S.C. §119(e) of U.S. Provisional Application Ser. No. 61/944,235, filed Feb. 25, 2014, the disclosure of which is incorporated herein by reference.

GOVERNMENT RIGHTS

This invention was made with government support under grant number CHE1149443 awarded by the National Science Foundation. The Government has certain rights in the invention.

TECHNICAL FIELD

The present disclosure relates to solid-phase azide supports, methods for making solid-state azide supports, and methods for capturing alkynes using the same. The present disclosure also relates to kits for solid-phase azide supports.

BACKGROUND

Natural products contain a wide variety of functional groups with varying reactivity. These moieties include some that are nucleophilic (amine, thiol, etc.) and others that are electrophilic (ketones, aldehydes, epoxides, lactones, etc.). There are a number of techniques developed for the isolation of natural products that contain these reactive functional groups. For example, the chemoselective purification of natural products that contain the hydroxyl or the carboxylic acid functional group has been described. However, these functional groups are highly prevalent in a crude natural product extract and upon purification a large pool of molecules still remains. Also, the hydroxyl and carboxylic enrichment tags may find less utility for the discovery of unknown molecules.

There are fewer methods, especially chemoselective techniques, which can target less reactive functional groups such as alkenes and alkynes. For example, the alkyne moiety has only been identified in a few natural product classes, and is predominantly produced by plants or marine organisms. There are a number of biologically interesting natural products that contain a terminal alkyne moiety. Alkynes are often in very low abundance but are often important for the bioactivity of the natural product.

One method for their isolation is by cobalt complexes that can be formed with either terminal or internal alkynes with the complex subsequently disassociated by oxidizing reagents. This cobalt-based strategy has been utilized the enrichment of alkyne-functionalized glycolipids. Dicobaltoctacarbonyl can form complexes with both terminal and internal alkynes, often under thermal conditions. The resulting dicobalt complex can then be reacted with diphenylphosphine, which is linked to a solid support to facilitate compound enrichment. All molecules not containing an alkyne moiety can be rinsed away, and the cobalt-alkyne complex can be disrupted using an oxidizing agent, such as iron nitrate yielding the alkyne-containing compounds. However, such methods may lead to unintended transformations when the cobalt-alkyne complex reacts with diphenylphosine, the oxidation conditions required for alkyne release may be be harsh, and inorganic salt may make analysis of the enriched molecules by LC-MS difficult.

Alkynes also react with trimethylsilane (TMS). The acidic terminal alkyne hydrogen can be removed with a strong base and addition of chlorotrimethylsilane yields the TMS-protected alkyne. However, the oxophilic nature of silicon may prevent the capture of alkynes over hydroxyls or carboxylic acids, and the base required for the deprotonation of the terminal alkyne may be too strong and cause unintended degradation of labile natural products. Furthermore, traditional alkyne purification procedures may lead to degradation of reactive functional groups.

As such, there exists an unmet need for the development of a tag to enrich compounds containing this relatively uncommon moiety.

As described herein, it has been discovered that certain solid-phase azide supports find utility in the isolation of alkyne containing compounds from various sources.

SUMMARY

In one aspect, the disclosure provides a functionalized solid support comprising the formula

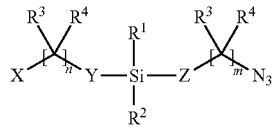

wherein:

X is a solid support;

Y is oxygen or —C($R^3$)($R^4$)_;

Z is oxygen or —C($R^3$)($R^4$)_;

$R^1$ and $R^2$ are in each instance independently selected from the group consisting of n-propyl, isopropyl, butyl, isobutyl, sec-butyl, tert-butyl, and optionally substituted aryl;

$R^3$ and $R^4$ are in each instance independently selected from the group consisting of hydrogen, methyl, ethyl, n-propyl, isopropyl, butyl, isobutyl, and sec-butyl;

n is an integer from 0 to 4; and m is an integer from 3 to 6.

In some embodiments of this aspect, X is a polystyrene bead. In some embodiments, $R^1$ and $R^2$ are independently selected from the group consisting of phenyl and isopropyl. In some embodiments, $R^1$ and $R^2$ are isopropyl. In some embodiments, Y is —$CH_2$—. In some embodiments, n is 2. In some embodiments, Z is oxygen. In some embodiments, m is 4.

In other embodiments of this aspect, $R^1$ and $R^2$ are phenyl. In some embodiments, Y is —C($R^3$)($R^4$)— and $R^3$ and $R^4$ independently selected from the group consisting of methyl, ethyl, and n-propyl. In some embodiments, n is 0.

In another embodiment of this aspect, the disclosure provides a functionalized solid support comprising the formula

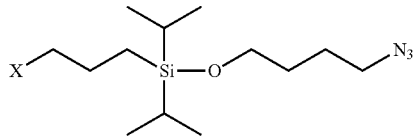

wherein X is a polystyrene bead.

In another aspect, the disclosure provides a functionalized solid support comprising the formula

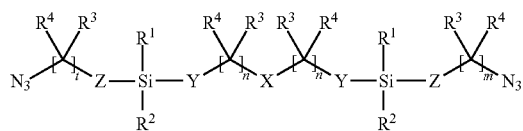

wherein:
X is a solid support;
each Y is independently oxygen or —C(R$^3$)(R$^4$)_;
each Z is independently oxygen or —C(R$^3$)(R$^4$)_;
R$^1$ and R$^2$ are in each instance independently selected from the group consisting of n-propyl, isopropyl, butyl, isobutyl, sec-butyl, tert-butyl, and optionally substituted aryl;
R$^3$ and R$^4$ are in each instance independently selected from the group consisting of hydrogen, methyl, ethyl, n-propyl, isopropyl, butyl, isobutyl, and sec-butyl;
each n is an integer from 0 to 4;
m is an integer from 3 to 6; and
t is an integer from 3 to 6,
wherein m and t are different integers.

In some embodiments of this aspect, X is a polystyrene bead. In some embodiments, R$^1$ and R$^2$ are independently selected from the group consisting of phenyl and isopropyl. In some embodiments, R$^1$ and R$^2$ are isopropyl. In some embodiments, Y is —CH$_2$—. In some embodiments, n is 2. In some embodiments, Z is oxygen. In some embodiments, m is 4 and t is 5.

In another embodiment of this aspect, the disclosure provides a functionalized solid support of claim 13 comprising the formula

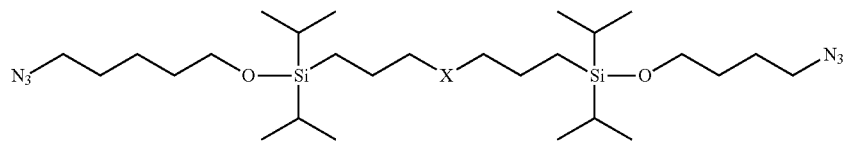

wherein X is a polystyrene bead.

In another aspect, the disclosure provides a process for isolating an alkyne containing compound, the process comprising the steps of
(a) contacting the alkyne containing compound with the functionalized solid support of claim 1 in the presence of a copper (I) catalyst to provide a bead-supported triazole compound; and
(b) contacting the bead-supported triazole compound with a fluoride source to release a free alcohol.

In some embodiments, the copper (I) catalyst is formed by contacting CuSO$_4$ with sodium ascorbate. In some embodiments, sodium ascorbate is added to a mixture of the alkyne containing compound and CuSO$_4$. In some embodiments, the fluoride source is HF. In some embodiments, the contacting step occurs for 1 to 3 hours. In some embodiments, the process further comprises the step of washing the bead-supported triazole compound with one or more of tetrahydrofuran, dichloromethane, toluene, dimethylformamide, hexanes, and dimethysulfoxide. In some embodiments, the process further comprises the step of washing the bead-supported triazole compound with tetrahydrofuran, dichloromethane, toluene, dimethylformamide, hexanes, and dimethysulfoxide.

In some embodiments of this aspect, the disclosure provides a process for isolating alkyne containing compound, the process comprising the steps of
(a) contacting the alkyne containing compound with a functionalized solid support comprising the formula

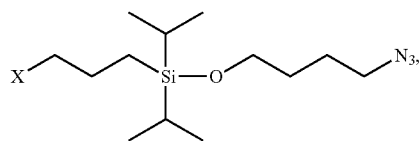

wherein X is a polystyrene bead;
(b) contacting the mixture of step (a) with CuSO$_4$;
(c) contacting the mixture of step (b) with sodium ascorbate to provide a bead-supported triazole compound;
(d) washing the bead-supported triazole with tetrahydrofuran, dichloromethane, toluene, dimethylformamide, hexanes, and dimethysulfoxide; and
(e) contacting the bead-supported triazole with HF to release a free alcohol.

In another aspect, the disclosure provides a process for isolating an alkyne containing compound, the process comprising the steps of
(a) contacting the alkyne containing compound with the compound of claim 13 in the presence of a copper (I) catalyst to provide a bead-supported triazole compound; and

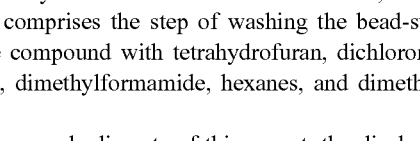

(b) contacting the bead-supported triazole compound with a fluoride source to release a free alcohol.

In some embodiments, the copper (I) catalyst is formed by contacting CuSO$_4$ with sodium ascorbate. In some embodiments, sodium ascorbate is added to a mixture of the alkyne containing compound and CuSO$_4$. In some embodiments, the fluoride source is HF. In some embodiments, the contacting step occurs for 1 to 3 hours. In some embodiments, the process further comprises the step of washing the bead-supported triazole compound with one or more of tetrahydrofuran, dichloromethane, toluene, dimethylformamide, hexanes, and dimethysulfoxide. In some embodiments, the process further comprises the step of washing the bead-supported triazole compound with tetrahydrofuran, dichloromethane, toluene, dimethylformamide, hexanes, and dimethysulfoxide.

In some embodiments of this aspect, the disclosure provides a process for isolating alkyne containing compound, the process comprising the steps of (a) contacting the alkyne containing compound with a functionalized solid support comprising the formula

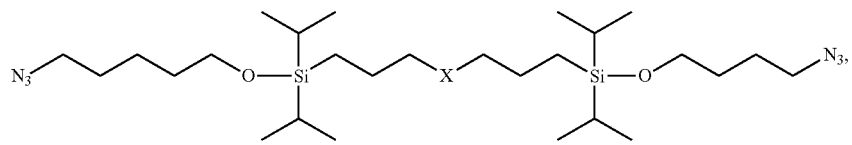

wherein X is a polystyrene bead;
(b) contacting the mixture of step (a) with CuSO$_4$;
(c) contacting the mixture of step (b) with sodium ascorbate to provide a bead-supported triazole compound;
(d) washing the bead-supported triazole with tetrahydrofuran, dichloromethane, toluene, dimethylformamide, hexanes, and dimethysulfoxide; and
(e) contacting the bead-supported triazole with HF to release a free alcohol.

DEFINITIONS

Figure 1:
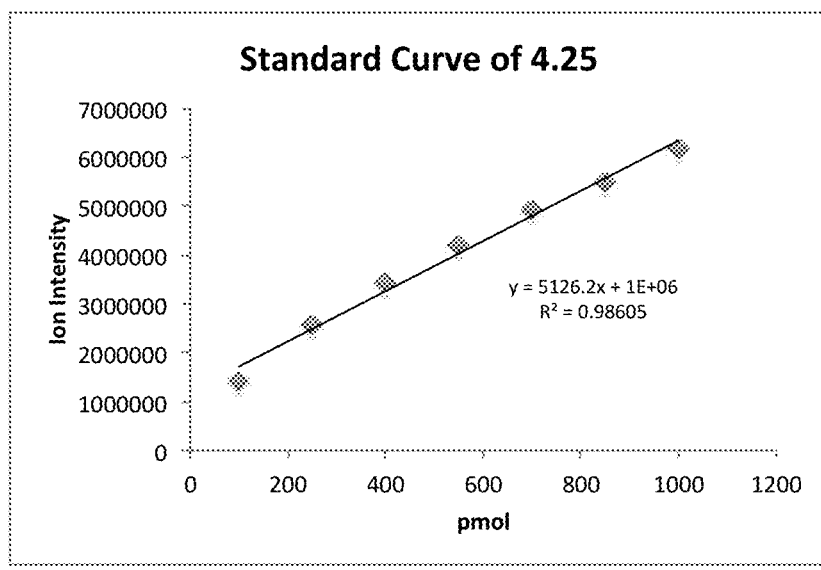
FIG. 1 is a graph generated by injecting increasing amounts of the standard triazole (4.25) into a LC-MS-TOF and plotting the corresponding pmol value against its observed ion intensity.

As used herein, the term "alkyl" includes a chain of carbon atoms, which is optionally branched. It is to be further understood that in certain embodiments, alkyl is advantageously of limited length, including $C_1$-$C_{12}$, $C_1$-$C_8$, $C_1$-$C_6$, and $C_1$-$C_4$. Illustratively, such particularly limited length alkyl groups, including $C_1$-$C_8$, $C_1$-$C_6$, and $C_1$-$C_4$, and the like may be referred to as "lower alkyl." Illustrative alkyl groups include, but are not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl, and the like.

The term "aryl" refers to an all-carbon monocyclic or fused-ring polycyclic groups of 6 to 14 carbon atoms ($C_6$-$C_{14}$) having a completely conjugated pi-electron system. Aryl includes all-carbon monocyclic or fused-ring polycyclic groups of 6 to 10 carbon atoms (e.g. "$C_6$-$C_{10}$ aryl"). Examples, without limitation, of aryl groups are phenyl, naphthalenyl and anthracenyl. The aryl group may be substituted as described above for alkyl or unsubstituted The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

As used herein, the terms "optionally substituted aryl" means the replacement of hydrogen atoms with other functional groups on and aryl ring. Such other functional groups illustratively include, but are not limited to, amino, hydroxy, halo, thio, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like.

As used herein, the term "solid support" refers to insoluble, functionalized, polymeric material to which reagents may be attached (often via a linker) allowing them to be readily separated (by filtration, centrifugation, etc.) from excess reagents, soluble reaction by-products or solvents. Suitable solid supports can be any known to one of skill in the art. Examples of solid supports include, but are not limited to, cross-linked polystyrene resins, polyamide resins, Tenta-Gel® resins, and the like. Suitable solid supports can be based on a polystyrene resin. For example, resin supports can include spherical beads of lightly cross linked gel type polystyrene (1-2% divinylbenzene) and poly(styrene-oxyethylene) graft copolymers which are functionalised to allow attachment of linkers and substrate molecules (e.g. polystyrene beads). It will be appreciated that the polystyrene bead can be of any type known to one of skill in the art, and such polystyrene bead is not limited to those mentioned in the present disclosure. The functionalized solid supports described herein are also generally referred to as solid-phase azide supports or solid-phase azide resins.

DETAILED DESCRIPTION

Throughout this disclosure, various publications, patents and patent applications are referenced. The disclosures of these publications, patents and applications in their entireties are hereby incorporated by reference into this disclosure.

Alkynes are capable of undergoing a variety of chemical reactions. One such reaction performed on alkynes is coupling with an azide in the presence of a copper(I) catalyst (the so-called "click chemistry" reaction). By way of example and without being bound by theory, it is thought that an azide and an alkyne form a triazole according to the mechanism shown in Scheme 1

Scheme 1

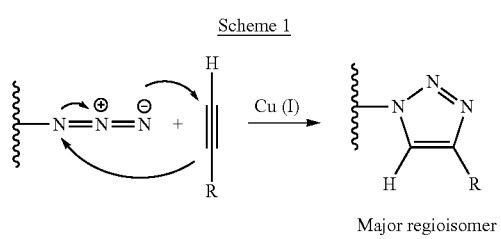

Major regioisomer

Despite the popularity of click chemistry, there are few reports of the use of triazole formation for the immobilization of small molecules onto solid-phase resin. Such strategies have been primarily utilized in the context of solid phase synthesis, and often require the use of linkers that can only be cleaved under harsh conditions, such as trifluoroacetic acid (TFA). Such harsh conditions make these approaches inapplicable to the isolation of natural products due to the sensitivity of many functional groups on natural products. Such an approach is summarized by Scheme 2.

Scheme 2

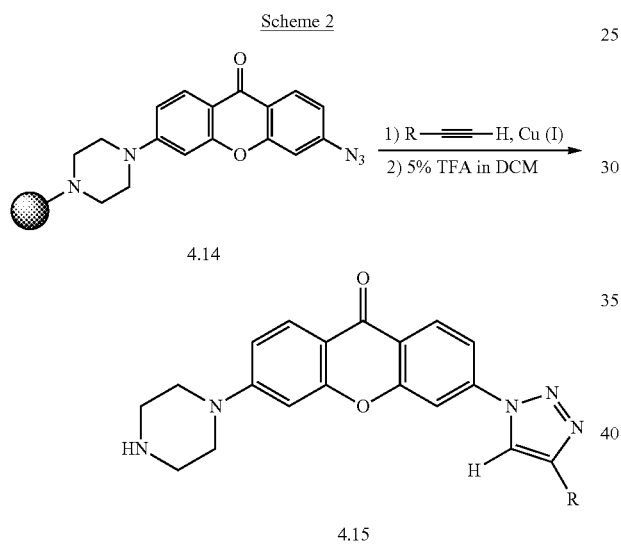

Solid-phase azide resins, and analogs and derivatives thereof, are described herein. The resins include a silyl group and two linkers that covalently attach an azide to the silyl group and the silyl group to a solid support. The solid-phase azide resins described herein may be used to capture alkynes under certain conditions and release the alkynes under other conditions, as described hereinbelow.

In one illustrative embodiment of the invention, the solid-phase azide resins may be used as a solid phase tool for the discovery of alkyne-containing natural products. The azide that is attached to the resin may undergo a 1,3-dipolar cycloaddition, more commonly called a click reaction, with a terminal alkyne present in a natural product, forming a triazole. The captured molecules can then be released from the solid phase support yielding the tagged natural product. In some embodiments, the resins and click conditions of the present disclosure were able to capture a wide variety of alkynes with an average enrichment yield of 90%. This tool may be used to discover novel natural products that have previously not been detected because of their low abundance or instability.

The solid-phase azide resins of the present disclosure, as referred to as alkyne-trapping agents, react with alkynes irreversibly in a chemoselective manner under mild conditions. Following reaction of the alkynes with the resins, the products may be released in a manner producing compounds that are substantially intact. Thus, the formulations provide the ability to detect alkyne-containing compounds. In some embodiments, the tagging strategy disclosed herein readily facilitates the discovery of natural products. Detection of a triazole product disclosed herein rather than free alkyne natural product may prevent degradation while not using traditional purification procedures.

In some embodiments, the solid-phase azide resin is a functionalized solid support comprising the formula

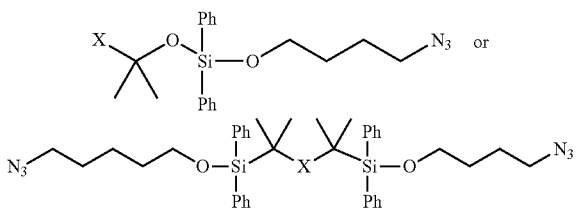

wherein X is a polystyrene bead.

In some embodiments, $R^3$ and $R^4$ are both substituted such that one or more of the linkers is a sterically encumbered linker and X and Y are both oxygen. In these embodiments, the solid-phase azide resin is a stable disiloxane resin for better loading capacity.

In some embodiments, $R^3$ and $R^4$ are both hydrogen adjacent to X and Y such that the one or more of the linkers is small for ease of synthesis on a scale of greater than 5 grams.

In some embodiments, the solid-phase azide resins disclosed herein are synthesized from a resin containing an electrophilic silyl group of the formula

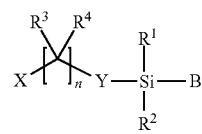

wherein B is a leaving group. The leaving group may be activated. In some embodiments the leaving group is para-methoxyphenyl and is activated by the addition of triflic acid. In other embodiments, the leaving group is halide, sulfonate, and the like.

In some embodiments, the nucleophile is

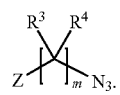

For example, the nucleophile may be

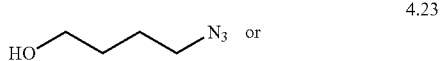

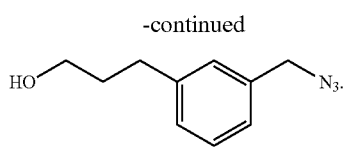

4.48

The functionalized solid support of the present disclosure may be used in a process for isolating an alkyne containing compound. The alkyne containing compound may be an internal or terminal alkyne. In some embodiments, the alkyne containing compound is isolated from several compounds, including component that do not contain alkyne groups, and may be in low abundance. In further embodiments, the alkyne containing compound contains sensitive functional groups that are not affected by the processes disclosed herein. For example, the alkyne containing compound may be exposed to the conditions described herein without substantial decomposition.

In some embodiments, the process of the present disclosure includes contacting the alkyne containing compound with the solid-phase azide resins described herein in the presence of a copper (I) catalyst to provide a bead-supported triazole compound. The copper (I) catalyst may be added directly to the reaction as a copper (I) salt, such as CuI, CuBr, etc; or may be formed in situ. In some embodiments, copper (I) is formed in situ from a combination of $CuSO_4$ and sodium ascorbate. It is to be appreciated that various copper sources and reducing agents may be utilized.

It will be appreciated that the amount of the copper source may be varied. In some embodiments, about 0.2, about 0.4, about 0.8, or about 1.0 molar equivalents of the copper source (relative to the resin loading capacity) are used with the process described herein. In further embodiments, about 0.2 to about 1.0 molar equivalents of the copper source are used. When a reducing agent is used, the amount of the reducing agent may be varied It will be appreciated that various solvent systems compatible with click chemistry, polystyrene resin, and the silyl ether are utilized. Also, it will be appreciated that the source of copper, reducing agent, and equivalents of each relative to the resin can be varied.

In another embodiment, copper (I) can be introduced directly to the reaction in the form of CuBr or CuI. Alternatively, a copper (II) salt mixed with reducing agent can be used to form copper (I) in situ. Application of click chemistry on solid phase favored may comprise the use of reduced copper and include conditions such as CuI and ascorbic acid in dimethylformamide (DMF)/piperdine (4:1) at room temperature, dichloromethane instead of DMF, or a mixture of DMF, tetrahydrofuran (THF), and diisopropylethylamine at 35° C. These conditions provided yields of 10-20%.

In some embodiments, the catalyst is copper sulfate. Illustratively, coupling occurs with 5 mol % copper (II) sulfate ($CuSO_4$) and 10 mol % of sodium ascorbate at room temperature. The solvents comprise THF, in which polystyrene beads swell, and addition of a minimal amount of water.

When the copper (I) catalyst is formed by contacting $CuSO_4$ with sodium ascorbate, the sodium ascorbate is preferably added to a mixture of the alkyne containing compound and $CuSO_4$.

The functionalized solid supports and process for isolating alkyne containing compounds as described herein can be illustrated according to the following Scheme 3.

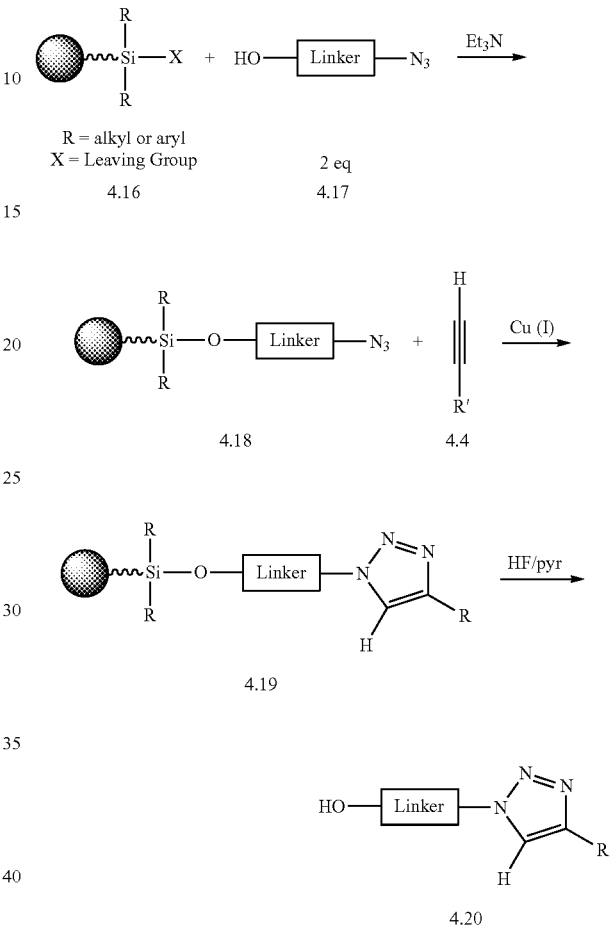

Briefly, a polystyrene bead can be functionalized with an activated dialkylsilane (4.16) that is subsequently conjugated to a linker that contains both a primary hydroxyl and an azide moiety (4.17). The hydroxyl forms a silyl ether bond with the resin, leaving the terminal azide available for click chemistry (4.18). After natural product (4.4) is captured by formation of a triazole (4.19), the resin is rinsed and cleaved with a mild reagent, such as HF.pyridine, releasing the newly formed triazole-functionalized natural product (4.20).

The formation of the bead-supported triazole can take place over various amounts of time. In some embodiments, the triazole is allowed to form for about 0 to about 24 hours, more preferably, 0.5 to 12 hours, still more preferably 1 to 6 hours, and most preferably 1 to 3 hours.

In some embodiments, the process of the present disclosure includes washing the bead-supported triazole compound with one or more of tetrahydrofuran, dichloromethane, toluene, dimethylformamide, hexanes, and dimethysulfoxide. The compounds may be added to the resins individually or in combination and may be added in any order.

In some embodiments, the process of the present disclosure includes contacting the bead-supported triazole compound with a fluoride source to release a free alcohol. The fluoride source may be HF, TBAF, etc. Alternative, other compounds known for reacting with silicon, such as pyridinium p-toluenesulfonate may be employed to release the free alcohol.

The general procedure for click chemistry of model alkynes with an azido resin can be achieved as follows. A mixture comprising one or more alkynes can be dissolved and added to a resin. A copper catalyst can be dissolved in solvent comprising water. The copper solution can be added to the alkyne mixture. The resin mixture can be agitated at room temperature.

In some embodiments, the process of the present disclosure is a process for isolating an alkyne containing compound that includes the steps of contacting the alkyne containing with a solid support comprising the formula

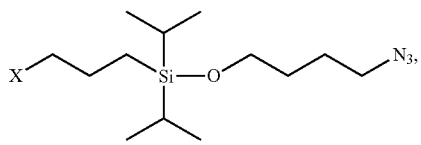

wherein X is a polystyrene bead to provide a first mixture, contacting the first mixture with CuSO$_4$ to provide a second mixture, contacting the second mixture with sodium ascorbate to provide a bead-supported triazole compound, washing the bead-supported triazole with tetrahydrofuran, dichloromethane, toluene, dimethylformamide, hexanes, and dimethylsulfoxide, and contacting the bead-supported triazole with HF to release a free alcohol.

In some embodiments, the process of the present disclosure is a process for isolating an alkyne containing compound that includes the steps of contacting the alkyne containing with a solid support comprising the formula

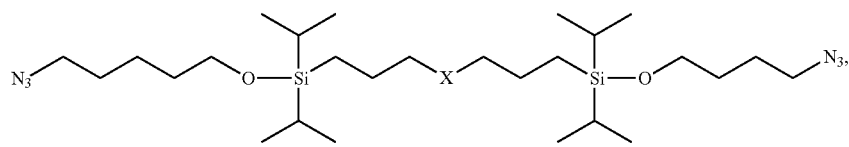

wherein X is a polystyrene bead to provide a first mixture, contacting the first mixture with CuSO$_4$ to provide a second mixture, contacting the second mixture with sodium ascorbate to provide a bead-supported triazole compound, washing the bead-supported triazole with tetrahydrofuran, dichloromethane, toluene, dimethylformamide, hexanes, and dimethylsulfoxide, and contacting the bead-supported triazole with HF to release a free alcohol.

In some embodiments, the solid-phase azide resin is designed to discover natural products that contain internal alykens using a ruthernium catalyst instead of a copper catalyst with a benzylic azide coupled to the resin. For example, the benzylic acid resin may be formed by replacing 4.23 with benzilic azide 4.48

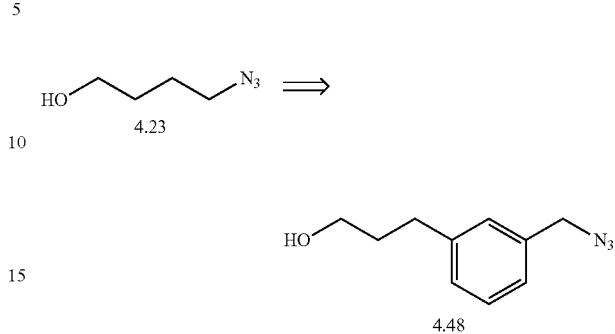

and reacting it with the resin-supported silyl chlorides described herein. Such a solid-phase azide resin could be used with or without solid-phase azide resin 4.30 to discover internal alkynes or both internal and terminal alkynes, respectively.

In some embodiments, the solid-phase azide resin is washed and cleaved with HF.pyridine/pyridine to release triazoles. In some embodiments, the cleaved molecules are subjected to LC-MS for quantitation. In some examples, 2×: 0.2 equiv. CuSO$_4$, 0.4 equiv. sodium ascorbate relative to resin loading capacity is used.

The majority of click chemistry conditions in the literature utilize a significant amount of water to assist with the solubility of both the metal and reducing agents (e.g., sodium ascorbate). Water can readily cause premature hydrolysis of the silyl ether linker. In addition, our previous work has shown that maximal loading capacities can be achieved with polystyrene-based resins; however, these scaffolds do not swell in water. It will be appreciated that efficient capture can be achieved by using minimal amounts of water in an organic solvent in connection with the processes set forth in the present disclosure.

It will be appreciated that the target alkyne for isolation by the solid-phase azide resins and methods describes herein, can be any alkyne from any source, without limitation. In some embodiment, the alkynes isolated are natural products from sources such as plants or marine organisms. In some embodiments, the alkynes are from, for example, marine actinomyces. Exemplary marine actinomyces include but are not limited to

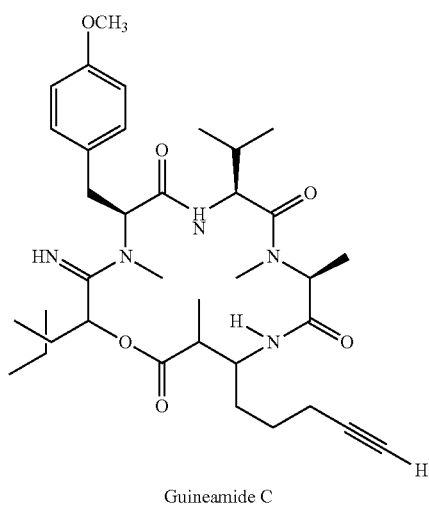
Guineamide C

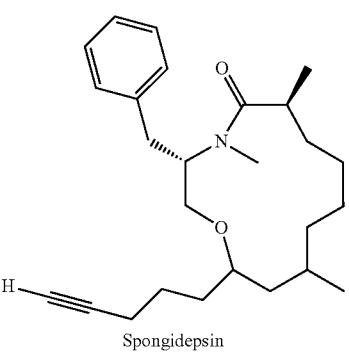
Spongidepsin

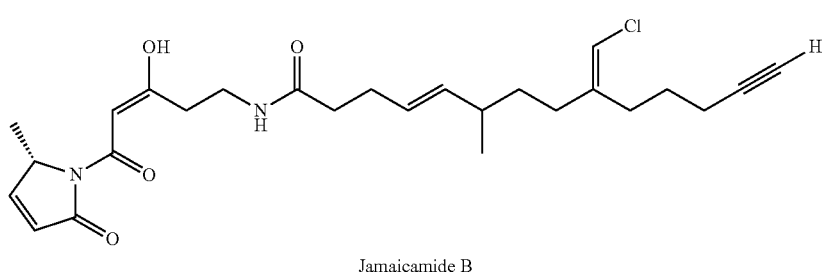
Jamaicamide B

The following examples further illustrate specific embodiments of the invention; however, the following illustrative examples should not be interpreted in any way to limit the invention.

EXAMPLES

The following examples are offered to illustrate but not to limit the invention. One of skill in the art will recognize that the following synthetic reactions and schemes may be modified by choice of suitable starting materials and reagents in order to access other compounds.

ABBREVIATIONS

The examples described herein use materials, including but not limited to, those described by the following abbreviations known to those skilled in the art:

| Abbreviation | Name |
|---|---|
| TLC | thin layer chromatography |
| DCM | dichloromethane |
| DMSO | dimethylsufoxide |
| TEA | triethylamine |
| THF | tetrahydrofuran |
| DMF | N,N-dimethylformamide |
| ACN | acetonitrile |
| PBS | phosphate buffered silane |

General Experimental Procedures and Materials:

All resin reactions were performed in fritted vessels (Biospin vessels from Biorad) under an inert atmosphere of Ar or $N_2$. All resins were obtained from EMD Biosciences. All alcohol-containing molecules were obtained from VWR or Sigma-Aldrich and used without further purification. Solvents were obtained from EMD Biosciences as anhydrous and not further purified. TEA was obtained from Sigma-Aldrich and was distilled over barium oxide under Ar.

Sample analysis was performed on an Agilent 1200 LC-MS-TOF using a reverse phase column (ZORBAX Eclipse Plus C18, Rapid Resolution HT, 1.8 micron, 2.1×50 mm) detected by electrospray ionization (positive ion mode). All samples and standard curve analysis was initiated with an isocratic elution of 100% A at 0.5 mL/min for 1 min followed by a linear gradient of 0-100% B at 0.5 mL/min over 5 min, then an isocratic elution for 1 min at 100% B, and re-equilibration with 100% A for 4 min (A: 95:5 $H_2O:CH_3CN$, 0.1% ammonium acetate; B 95:5 $CH_3CN:H_2O$, 0.1% ammonium acetate). Fragmentation voltages ranged from 75V to 175V, which was determined on a molecule-by-molecule basis. Sample analysis was also performed on an Agilent 6540 LC-CID-MS-QTOF using a reverse phase column (ZORBAX Eclipse Plus C18, Rapid Resolution HT, 1.8 micron, 2.1×50 mm) detected by electrospray ionization (positive ion mode). All sample analysis was initiated with an isocratic elution of 100% A at 0.4 mL/min for 2 min followed by a linear gradient of 0-100% B at 0.4 mL/min over 5 min, then an isocratic elution for 1 min at 100% B, and re-equilibration with 100% A for 2 min (A: 95:5 $H_2O:CH_3CN$, 0.1% ammonium acetate; B 95:5 $CH_3CN:H_2O$, 0.1% ammonium acetate). Fragmentation spectra were obtained with collision cell voltages of 25V. Gel-Phase $^{13}C$ nuclear magnetic resonance (NMR) spectra (Meloni, M. M.; et al. *Tetrahedron* 2007, 63, 299-311) were recorded on a Varian I500 or a Varian VXR-400 and chemical shifts were determined relative to residual solvent peaks in parts per million. Infrared spectroscopy (IR) was recorded using a Perkin Elmer Spectrum One FT-IR and a KBr pellet.

Example 1

Synthesis of 4-Azidobutyl Acetate (4.22)

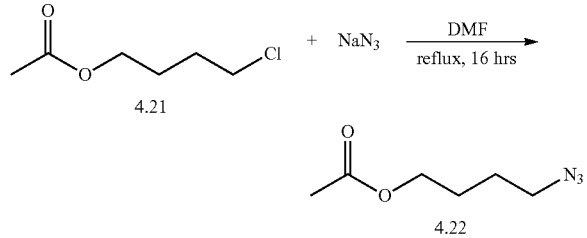

To a 500 mL flask was added 5.0 g (33 mmol, 1.0 eq) of 4-chlorobutylacetate and dissolved in 100 mL of DMF. Next 2.6 g (40 mmol, 1.2 eq) of sodium azide was added by a glass pipette. A water condenser was placed onto the flask and the reaction heated to 80° C. for 16 hr with stirring. The reaction was then cooled to room temperature and quenched with 300 mL of water to dissolve the sodium salts. The aqueous solution was extracted with diethyl ether 3×100 mL. The organic layers were combined and dried with MgSO$_4$. The solution was filtered and concentrated under vacuum with no external heat, resulting in 4-azido-1-butylacetate (4.22), which was carried onto the next step without further purification; $^1$H NMR (CDCl$_3$, 300 MHz): δ: 4.04 (t, J=6.0 Hz, 2H), 3.27 (t, J=6.2 Hz, 2H), 2.00 (s, 3H), 1.76-1.52 (m, 4H). $^{13}$C NMR (75 MHz, CDCl$_3$) δ: 170.82, 63.55, 50.84, 25.73, 25.39, 20.73. 81% yield, clear oil.

Example 2

Synthesis 4-azido-1-butanol (4.23)

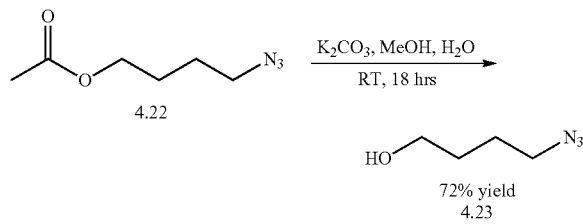

5.1 g of 4-azido-1-butylacetate (4.22) (33 mmol, 1.0 eq) from Example 2 was dissolved in 30 mL of MeOH and 2 mL of water. This solution was then saturated with K$_2$CO$_3$ and stirred overnight at room temperature. The reaction was then checked by TLC to confirm conversion of the acetate to the primary hydroxyl. Water (300 mL) was added to dissolve the potassium salt and extracted with diethyl ether 3×100 mL. The organic extracts were combined and dried with MgSO$_4$. The solution was filtered and concentrated under vacuum with no external heat. 4.23: $^1$H NMR (300 MHz, Acetone-d$_6$) δ: 3.56 (t, J=6.1 Hz, 2H), 3.40-3.31 (m, 2H), 1.74-1.49 (m, 4H). $^{13}$C NMR (75 MHz, Acetone) δ: 61.90, 52.03, 49.82, 26.28. 71% yield, clear oil.

Example 3

Synthesis of Solid-Phase Azide Support 4.24

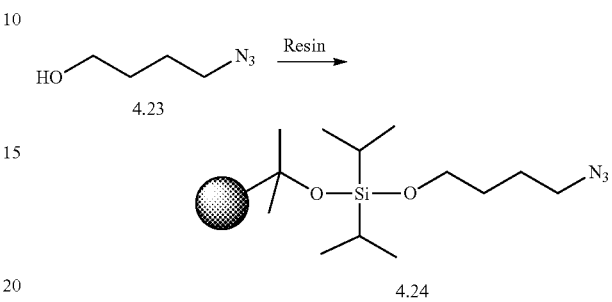

4-Azido-1-butanol (4.23) was coupled to the appropriate resin to form compound 4.24. Gel-phase $^{13}$C NMR confirmed that the resin was conjugated to the azido-linker.

Example 4

Coupling of 4-Azido-1-Butanol (4.23) to Resin 4.29 to Provide Solid-Phase Azide Support 4.30

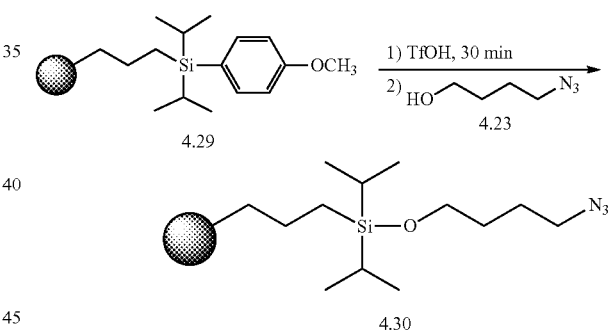

A 10 mL fritted polypropylene column was charged with 200 mg (0.28 mmol) of (4-methoxyphenyl)diisopropylsilypropyl polystyrene (loading capacity of 1.4 mmol/g) resin and equipped with a rubber septum. The resin was flushed with Ar for 10 min and then swollen in 3 mL of anhydrous DCM. Trifluoromethasnesulfonic acid (1.6 mmol, 6 eq) was added to the resin. The resin turned orange and was agitated at room temperature for 30 minutes. After resin activation, the resin was washed with 2 mL anhydrous CH$_2$Cl$_2$ three times all under Ar. The resin was reswollen in fresh DCM before coupling. With the triflated resin under Ar and swollen, 324 μL (1.1 mmol, 8.0) eq of freshly distilled triethylamine was added to the resin and the color of the resin changed from orange to colorless. 64 mg of 4.23 (0.56 mmol, 2 eq) was added neat to the resin vessel. The vessel was capped and agitated overnight at room temperature. After coupling, the resin was uncapped and rinsed with DCM×3 and THF×3. This resin was used without drying to avoid any degradation. For coupling of model alkynes, the resin was aliquoted into 5 eppitubes, each with 500 μL of THF and 40 mg of 4.30; $^{13}$C NMR (125 MHz, CD$_2$Cl$_2$) δ: 127.41, 62.65, 53.80, 51.43, 39.79, 30.04, 25.55, 17.53, 17.24, 12.99, 12.55.

Example 5

Standard Procedure for Click Chemistry of Model Alkynes with an Azido Resin A mixture comprising one or more alkynes is dissolved and added to a resin. A copper catalyst is dissolved in solvent comprising water. The copper solution is added to the alkyne mixture. The resin mixture is agitated at room temperature.

Example 6

Standard Resin Rinse Protocol

After being agitated with the alkyne mixture, resin is transferred to a fritted vessel and rinsed as follows: CH$_2$Cl$_2$ (suspend resin in 2 mL for 10 min, rinse 2×2 mL), THF (suspend resin in 2 mL for 10 min, rinse 2×2 mL), DMSO/CH$_2$Cl$_2$ (1:1, suspend resin in 2 mL for 10 min, rinse 2×2 mL), THF (suspend resin in 2 mL for 10 min, rinse 2×2 mL), DMSO/CH$_2$Cl$_2$ (1:1, suspend resin in 2 mL for 10 min, rinse 2×2 mL), CH$_2$Cl$_2$ (suspend resin in 2 mL for 10 min, rinse 2×2 mL), toluene (suspend resin in 2 mL for 5 min, rinse 2×2 mL), DMF (suspend resin in 2 mL for 5 min, rinse 2×2 mL), CH$_2$Cl$_2$ (suspend resin in 2 mL for 5 min, rinse 2×2 mL), hexanes (suspend resin in 2 mL for 5 min, rinse 2×2 mL), CH$_2$Cl$_2$/MeOH (3:1, suspend resin in 2 mL for 5 min, rinse 2×2 mL), and finally CH$_2$Cl$_2$ (3×2 mL).

Example 7

Release of Triazoles from Resin

After rinsing, the coupled resin is transferred to polypropylene vials (2 mL vials). To the resin is added 100 µL a freshly prepared solution of 400/50/50 µL (v/v) of THF/HF.pyridine (70/30 wt %)/pyridine (2 mmol of HF, 45 eq) and the reaction is gently agitated at room temperature for 3 hr. To this is then added 500 µL of TMSOMe (3.6 mmol, 83 eq) to quench excess HF and the resin was agitated for an additional 10 minutes at room temperature. The resin is then washed with THF (3×1 mL) followed by DCM (3×1 mL) and filtered over a 1 mL fritted polypropylene column into a 20 mL scintillation vial. The wash is then concentrated with no additional heating and the sample was dissolved in 5 mL of 2:1:1 H$_2$O/THF/MeOH for quantification.

Example 8

Synthesis of Triazole Standards 4.25, 4.26, 4.27, 4.42, 4.43, and 4.44

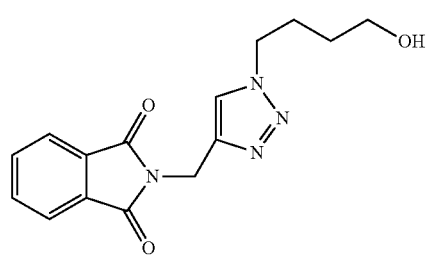
4.25

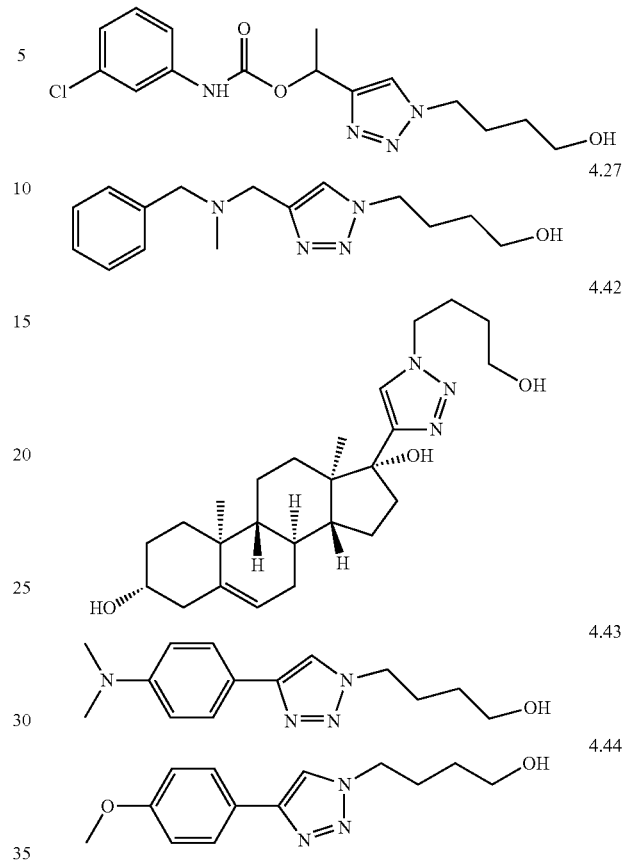

In a scintillation vial 100 mg (1 eq) of the alkyne was dissolved in 2 mL of THF and 1 mL of water followed by 1 eq of 4.23. After mixing, 0.2 eq of CuSO$_4$ was added followed by 0.4 eq of NaAsc. The reaction was allowed to stir overnight at room temperature. After analysis by TLC to confirm reaction completion, 5 mL of water was added and extract three times with 15 mL of DCM. The combined organic extracts were dried over MsSO$_4$, filtered, and concentrated. 4.25: $^1$H NMR (CD$_3$OD, 500 MHz): δ: =7.93 (s, 1H), 7-78-7.71 (m, 4H), 4.87 (s, 2H), 4.35 (t, J=5 Hz, 2H), 3.50 (t, J=5 Hz, 2H), 1.90 (m, 2H), 1.45 (m, 2H); $^{13}$C NMR (CD$_3$OD, 100 MHz): δ: =168.96, 135.53, 135.39, 133.20, 124.29, 124.20, 61.99, 51.21, 33.69, 30.27, 27.83; HRESIMS m/z [M+H]$^+$301.1290 (calcd for C$_{15}$H$_{16}$N$_4$O$_3$, 301.1297). 4.26: $^1$H NMR (CDCl$_3$, 400 MHz): δ: =7.88 (s, 1H), 7.63 (s, 1H), 7.57 (s, 1H), 7.25-7.20 (m, 2H), 7.02 (d, J=7.4 Hz, 1H), 6.03 (s, 1H), 4.38 (t, J=8 Hz, 2H), 3.34 (t, J=8 Hz, 2H), 2.00-1.95 (m, 2H), 1.72 (d, J=6 Hz, 3H), 1.53-1.41 (m, 2H); $^{13}$C NMR (CDCl$_3$, 100 MHz): δ: =152.84, 139.27, 129.87, 123.21, 118.62, 116.62, 65.57, 61.92, 61.46, 50.12, 29.14, 26.74, 19.65; HRESIMS m/z [M+H]$^+$261.1714 (calcd for C$_{15}$H$_{19}$ClN$_4$O$_3$, 261.1710). 4.27: $^1$H NMR (CDCl$_3$, 400 MHz): δ: =7.48 (s, 1H), 7.28-7.14 (m, 5H), 4.34 (t, J=8 Hz, 2H), 3.65 (s, 2H), 3.60 (t, J=8 Hz, 2H), 3.50 (s, 2H), 2.18 (s, 3H), 1.96-1.91 (m, 2H), 1.52-1.48 (m, 2H); $^{13}$C NMR (CDCl$_3$, 100 MHz): δ: =145.06, 138.30, 128.99, 128.18, 127.03, 122.51, 61.45, 61.36, 51.93, 49.99, 41.99, 29.17, 26.82; HRESIMS m/z [M+H]$^+$275.1851 (calcd for C15H22N4O, 275.1866). 4.42: $^1$H NMR (CD$_3$OD, 400 MHz): δ: =7.73 (s, 1H), 4.39 (t, J=7 Hz, 2H), 3.55 (t, J=7 Hz, 2H), 2.39-2.10 (m, 10H), 2.10-1.87 (m, 2H), 1.86-1.51 (m, 11H), 1.50-1.45 (m, 2H), 1.45 (s, 3H), 0.99 (s, 3H); $^{13}$C NMR (CD$_3$OD, 100 MHz): δ: =155.43, 142.16, 123.87, 122.29, 83.21, 72.33, 62.08, 51.44, 48.36, 47.87, 42.98, 38.51, 37.66, 34.21, 33.90, 32.70, 32.23, 30.90, 30.38, 28.04, 25.06, 21.80, 19.88, 14.75; HRESIMS m/z [M+H]$^+$430.3084 (calcd for C$_{25}$H$_{39}$N$_3$O$_3$, 430.3064) 4.43: $^1$H NMR (CD$_3$OD, 400 MHz): δ: =8.03, (s, 1H), 7.56 (d, J=9 Hz, 2H), 6.73 (d, J=9 Hz, 2H), 4.36 (t, J=7 Hz, 2H), 3.52 (t, J=7 Hz, 2H), 2.88 (s, 6H), 1.96-1.90 (m, 2H), 1.51-1.45 (m, 2H); $^{13}$C NMR (CDCl$_3$, 100 MHz): δ: =152.13, 149.71, 127.57, 120.57, 119.82, 113.79, 62.09, 51.21, 40.69, 30.40, 27.93; 4.44: $^1$H NMR ((CD$_3$)$_2$SO, 500 MHz): δ: =8.44 (s, 1H), 7.75 (d, J=9 Hz, 2H), 7.01 (d, Ji=9 Hz, 2H), 4.37 (t, J=7 Hz, 2H), 3.77 (s, 3H), 3.42 (t, J=7 Hz, 2H), 1.91-1.85 (m, 2H), 1.44-1.38 (m, 2H); $^{13}$C NMR ((CD$_3$)$_2$SO 125 MHz): δ: =158.89, 146.16, 126.40, 123.47, 120.23, 114.24, 59.99, 55.09, 49.48, 29.27, 26.52; HRESIMS m/z [M+H]$^+$248.1383 (calcd for C$_{13}$H$_{17}$N$_3$O$_2$, 248.1394).

Example 9

Calculation of Alkyne Enrichment Yields

Each solution-phase synthesized triazole was dissolved in 2:1:1 H$_2$O:MeOH:THF to yield the concentrations required to provide 1000 pmol, 700 pmol, 560 pmol, 420 pmol, 280 pmol, 140 pmol, and 1 pmol in separate 1 µL injections into the LC-MS-TOF. For all compounds, the optimal fragmentation voltage was determined by assessment of the 700 pmol injection at 50V, 100V, 125V, 150V, 175V, 200V, 225V, and 250V. The fragmentation voltage yielding the highest ion intensity was selected. Following this analysis, all samples were run at each optimal voltage determined for each compound included in the sample. Standard curves were generated for all model compounds by running two independent sets of samples. A representative graph is shown for

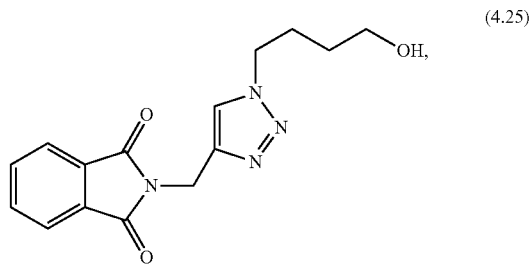 [SMILES: O=C1c2ccccc2C(=O)N1Cc1cn(CCCCO)nn1]

(4.25)

as shown in FIG. 1.

Unknown samples were quantified by comparison to the generated standard curves. All reactions were run in triplicate and averaged. Analysis of sample triazoles after release was performed by injection of 1 µL of the sample was dissolved in 5 mL of 2:1:1 H$_2$O/THF/MeOH onto a LC-MS-TOF and comparing the observed peak area to that of standard curve data.

Example 10

Evaluation of Copper (I) Salts

Following the procedure of Example 5, copper (I) can be introduced directly to the reaction in the form of CuBr or CuI. In one example, application of click chemistry on solid phase comprised the use of reduced copper and include conditions such as CuI and ascorbic acid in dimethylformamide (DMF)/piperdine (4:1) at room temperature, dichloromethane instead of DMF, or a mixture of DMF, tetrahydrofuran (THF), and diisopropylethylamine at 35° C. These conditions provided yields of 10-20%.

Example 11

Evaluation of Copper (II) Salt Mixed with Reducing Agent can be Used to Form Copper (I) In Situ Following the procedure of Example 5, copper sulfate was used as a copper source, along with sodium ascorbate. The resin used in this example was compound 4.24. The solvents comprised THF, in which polystyrene beads swell, and addition of a minimal amount of water.

The amount of catalyst was 2x, 0.2 equiv. CuSO$_4$, 0.4 equiv. sodium ascorbate, relative to resin loading capacity; 40 µL water and the reaction was allowed to run overnight. Any alkyne not captured was found in the resin drain and was collected and concentrated, while the resin was washed and cleaved to release any newly formed triazoles (HF.pyridine/pyridine). The drained and cleaved molecules were subjected to LC-MS for quantitation in yields from 3% to 10%. The resulting triazoles and their corresponding capture and release yields (yield of triazole from alkyne released during the release step as performed according to Example 7) are shown in Table 1.

TABLE 1

Yields of triazoles 4.25-4.27 utilizing resin 4.24, CuSO4, and sodium ascorbate.

| Model Triazole | Capture and Release Yield |
| --- | --- |
| 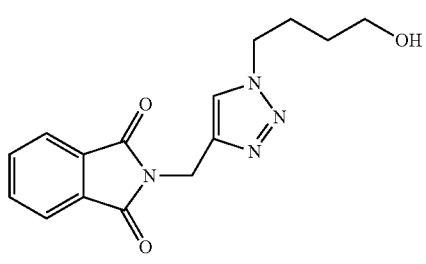 4.25 | 3% |

TABLE 1-continued

Yields of triazoles 4.25-4.27 utilizing resin 4.24, CuSO4, and sodium ascorbate.

| Model Triazole | Capture and Release Yield |
|---|---|
| 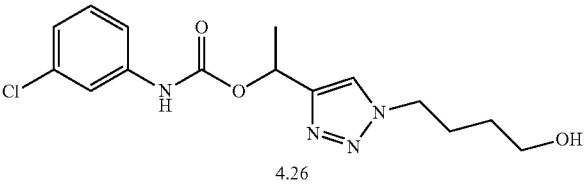 [SMILES: CC(OC(=O)Nc1cccc(Cl)c1)c1cn(CCCCO)nn1]<br>4.26 | 6% |
| 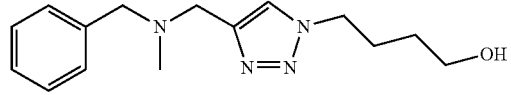<br>4.27 | 10% |

Example 12

Evaluation of Solvents and Buffering Conditions with Disiloxane Resins 4.24 and 4.28

In this example, the procedures of Example 5 and 11 were followed, except for the modifications detailed in this Example 12. Instead of dissolving the $CuSO_4$ and sodium ascorbate in water, phosphate buffered saline or PBS (pH=7.5) was utilized throughout this Example. Resins were varied by altering the groups about the silicon between isopropyl 4.24 and

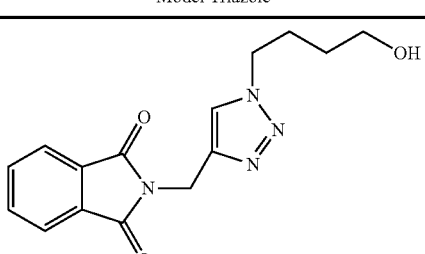

(resin 4.28)

the amount of $CuSO_4$ was varied from 0.2 eq to 0.4 eq, and the solvent was varied between THF and DMF as detailed below in Tables 2-11. In some examples trimethylamine was added as detailed below in Tables 2-11. The resulting triazoles and their corresponding yields for each set of conditions are shown in Tables 2-11.

TABLE 2

Yields of triazoles 4.25-4.27 utilizing resin 4.24, 0.2 eq CuSO4, 0.4 eq sodium ascorbate, 0.5 eq Et3N, and THF.

4.24

0.2 eq CuSO₄, 0.4 eq sodium ascorbate, 0.5 eq Et₃N, solvent: THF

| Model Triazole | Yield |
|---|---|
| 4.25 | 7% |

TABLE 2-continued
Yields of triazoles 4.25-4.27 utilizing resin 4.24, 0.2 eq CuSO4, 0.4 eq sodium ascorbate, 0.5 eq Et₃N, and THF.
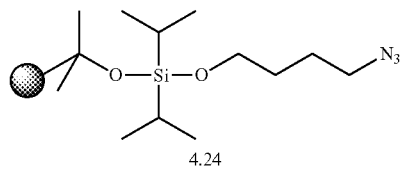 [SMILES: CC(C)[Si](OCCCCN=[N+]=[N-])(OC(C)(C)C)C(C)C]
4.24
| 0.2 eq CuSO₄, 0.4 eq sodium ascorbate, 0.5 eq Et₃N, solvent: THF | |
|---|---|
| Model Triazole | Yield |
| 4.26 | 75% |
| 4.27 | 19% |
| Average | 34% |
TABLE 3
Yields of triazoles 4.25-4.27 utilizing resin 4.24, 0.4 eq CuSO₄, 0.8 eq sodium ascorbate, and THF.
| 0.4 eq CuSO4, 0.8 eq sodium ascorbate, solvent: THF | |
|---|---|
| Model Triazole | Yield |
| 4.25 | 14% |
| 4.26 | 22% |
| 4.27 | 20% |
| Average | 19% |

TABLE 4
Yields of triazoles 4.25-4.27 utilizing resin 4.24, 0.2 eq CuSO$_4$, 0.4 eq sodium ascorbate, 0.5 eq Et$_3$N, DMF.
0.2 eq CuSO$_4$, 0.4 eq sodium ascorbate, 0.5 eq Et$_3$N solvent: DMF
| Model Triazole | Yield |
|---|---|
| 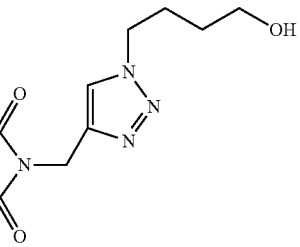<br>4.25 | 0% |
| 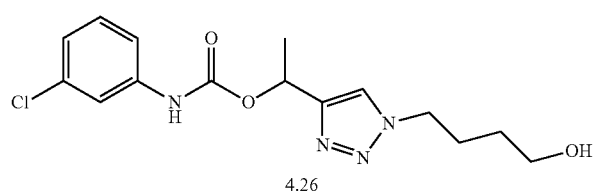 [SMILES: CC(OC(=O)Nc1cccc(Cl)c1)c1cn(CCCCO)nn1]<br>4.26 | 61% |
| 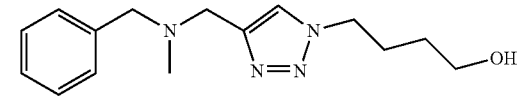<br>4.27 | 21% |
| Average | 27% |
TABLE 5
Yields of triazoles 4.25-4.27 utilizing resin 4.24, 0.2 eq CuSO$_4$, 0.4 eq sodium ascorbate, and DMF.
0.2 eq CuSO$_4$, 0.4 eq sodium ascorbate, solvent: DMF
| Model Triazole | Yield |
|---|---|
| 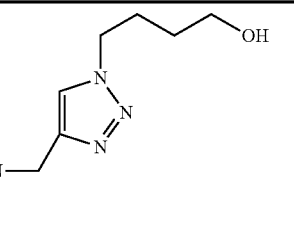<br>4.25 | 0% |
| 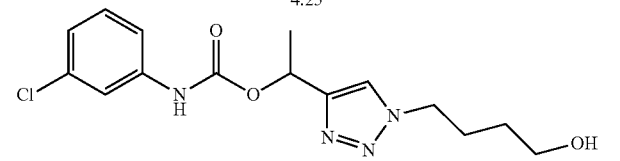<br>4.26 | 2% |
| 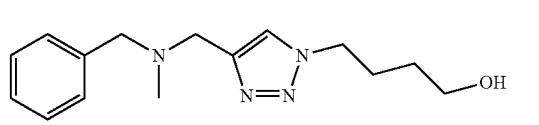<br>4.27 | 19% |
| Average | 7% |

TABLE 6
Yields of triazoles 4.25-4.27 utilizing resin 4.24, 0.4 eq CuSO$_4$, 0.8 eq sodium ascorbate, and DMF.
0.4 eq CuSO$_4$, 0.8 eq sodium ascorbate, solvent: DMF
| Model Triazole | Yield |
|---|---|
| 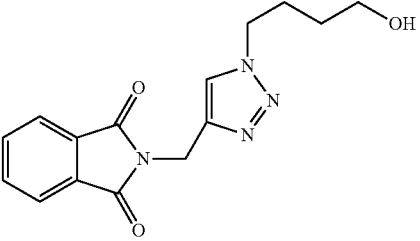 4.25 | 5% |
| 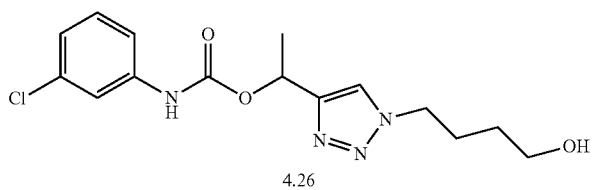 [SMILES: CC(OC(=O)Nc1cccc(Cl)c1)c1cn(CCCCO)nn1] 4.26 | 46% |
| 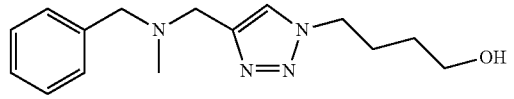 4.27 | 16% |
| Average | 22% |
TABLE 7
Yields of triazoles 4.25-4.27 utilizing resin 4.28, 0.2 eq CuSO$_4$, 0.4 eq sodium ascorbate, 0.5 eq Et$_3$N, and THF.
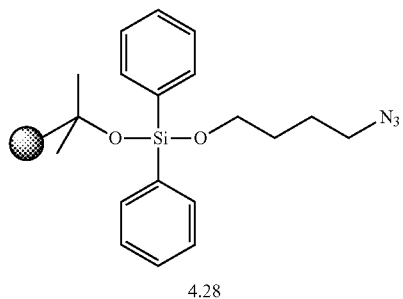 [SMILES: CC(C)(C)O[Si](OCCCCN=[N+]=[N-])(c1ccccc1)c1ccccc1]
4.28
0.2 eq CuSO4, 0.4 eq sodium ascorbate, 0.5 eq Et3N, solvent: THF
| Model Triazole | Yield |
|---|---|
| 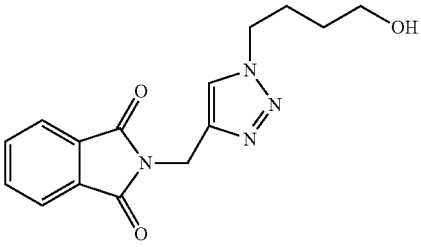 4.25 | 5% |

TABLE 7-continued
Yields of triazoles 4.25-4.27 utilizing resin 4.28, 0.2 eq CuSO$_4$, 0.4 eq sodium ascorbate, 0.5 eq Et$_3$N, and THF.
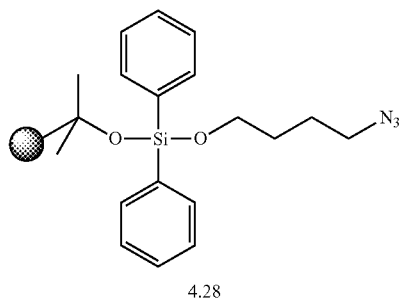
4.28
| 0.2 eq CuSO4, 0.4 eq sodium ascorbate, 0.5 eq Et3N, solvent: THF | |
|---|---|
| Model Triazole | Yield |
| 4.26 | 74% |
| 4.27 | 31% |
| Average | 37% |
TABLE 8
Yields of triazoles 4.25-4.27 utilizing resin 4.28, 0.4 eq CuSO$_4$, 0.8 eq sodium ascorbate, and THF.
| 0.4 eq CuSO$_4$, 0.8 eq sodium ascorbate, solvent: THF | |
|---|---|
| Model Triazole | Yield |
| 4.25 | 10% |
| 4.26 | 38% |

TABLE 8-continued

Yields of triazoles 4.25-4.27 utilizing resin 4.28, 0.4 eq CuSO$_4$, 0.8 eq sodium ascorbate, and THF.
0.4 eq CuSO$_4$, 0.8 eq sodium ascorbate, solvent: THF

| Model Triazole | Yield |
|---|---|
| 4.27 | 0% |
| Average | 16% |

TABLE 9

Yields of triazoles 4.25-4.27 utilizing resin 4.28, 0.2 eq CuSO$_4$, 0.4 eq sodium ascorbate, 0.5 eq Et$_3$N, and DMF.
0.2 eq CuSO$_4$, 0.4 eq sodium ascorbate, 0.5 eq Et$_3$N solvent: DMF

| Model Triazole | Yield |
|---|---|
| 4.25 | 16% |
| 4.26 | 59% |
| 4.27 | 58% |
| Average | 44% |

TABLE 10
Yields of triazoles 4.25-4.27 utilizing resin 4.28, 0.2 eq CuSO$_4$, 0.4 eq sodium ascorbate, and DMF.
0.2 eq CuSO$_4$, 0.4 eq sodium ascorbate, solvent: DMF
| Model Triazole | Yield |
|---|---|
| 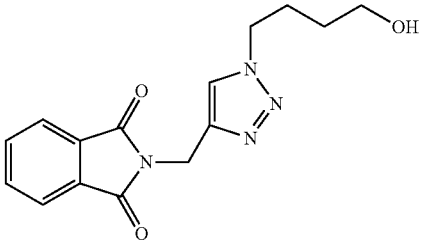<br>4.25 | 3% |
| 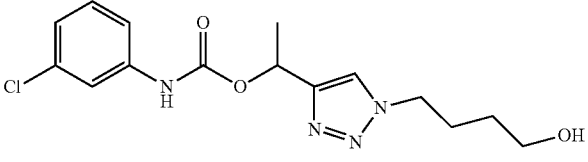<br>4.26 | 7% |
| 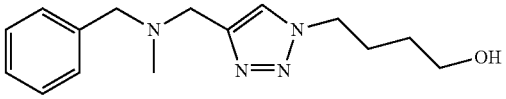<br>4.27 | 18% |
| Average | 9% |
TABLE 11
Yields of triazoles 4.25-4.27 utilizing resin 4.28, 0.4 eq CuSO$_4$, 0.8 eq sodium ascorbate, and DMF.
0.4 eq CuSO$_4$, 0.8 eq sodium ascorbate, solvent: DMF
| Model Triazole | Yield |
|---|---|
| 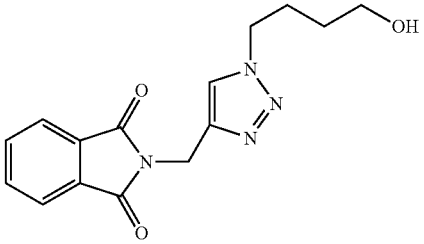<br>4.25 | 0% |
| 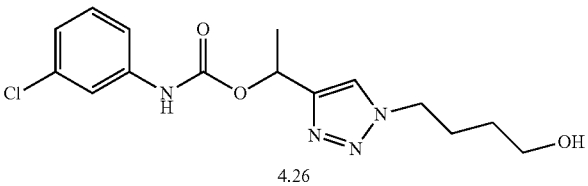 [SMILES: CC(OC(=O)Nc1cccc(Cl)c1)c1cn(CCCCO)nn1]<br>4.26 | 28% |

TABLE 11-continued

Yields of triazoles 4.25-4.27 utilizing resin 4.28, 0.4 eq CuSO₄, 0.8 eq sodium ascorbate, and DMF.
0.4 eq CuSO₄, 0.8 eq sodium ascorbate, solvent: DMF

| Model Triazole | Yield |
|---|---|
| 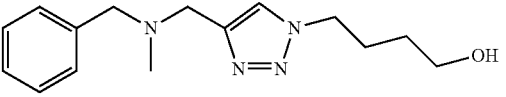 4.27 | 20% |
| Average | 16% |

Example 13

Evaluation of Solvents and Buffering Conditions with Siloxane Solid-Phase Azide Support 4.30

In this example, the procedures of Example 5 were utilized, except for the modifications detailed in this Example 13. Following the procedure of Example 5, copper sulfate was used as a copper source, along with sodium ascorbate. The resin used in this example was solid-phase azide support 4.30. The solvents comprised THF, in which polystyrene beads swell, and addition of a minimal amount of phosphate buffered saline or PBS (pH=7.5).

For two of the standard alkynes, nearly complete conversion to the triazole was obtained (4.25 and 4.27), the third (4.26) was converted to the triazole in a 44% yield. The resulting triazoles and their corresponding yields are shown in Table 12.

Example 14

Time Course Experiment with Solid-Phase Azide Support 4.30

In this example, the procedures of Examples 5 and 13 were utilized, except for the modifications detailed in this Example 14. Following the procedure of Example 5, copper sulfate (1.0 eq) was used as a copper source, along with sodium ascorbate (2.0 eq). The resin used in this example was solid-phase azide support 4.30. The solvents comprised THF, in which polystyrene beads swell, and addition of a minimal amount of phosphate buffered saline or PBS (pH=7.5).

Solid-phase azide support 4.30 was subjected to the click chemistry reagents and alkyne substrates for 1, 3, 6, 9, or 12 hrs. After the allotted reaction time, the resin was drained, rinsed, and cleaved. Analysis of both the drain and the

TABLE 12

Yields of triazoles 4.25-4.27 utilizing solid-phase azide support 4.30, CuSO₄, and sodium ascorbate.

| Model Triazole | Yield |
|---|---|
| 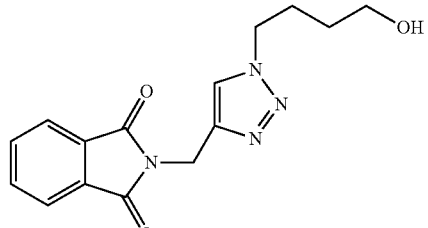 4.25 | 99% |
| 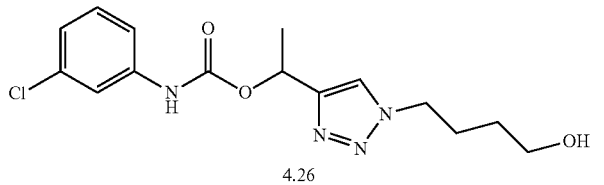 [SMILES: CC(OC(=O)Nc1cccc(Cl)c1)c1cn(CCCCO)nn1] 4.26 | 44% |
| 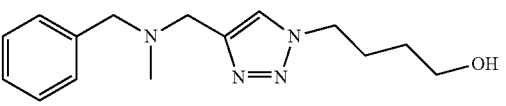 4.27 | 99% |
| Average | 67% | released pool was performed by LC-MS to determine the amount of alkyne capture and triazole in the drain, Table 13.

In this example, after one hour, about 76% of all model alkynes were captured and after three hours about 93% were converted to their corresponding triazole. Little to no premature cleavage (indicated by triazole in the drain) was seen in the 1, 3, or 6 hr coupling reactions. At the 9 hr time point, approximately 10% of the triazoles were detected in the drain, which increased to 43% at 12 hrs. The alkynes by conversion to a triazole in three hours with minimal loss due to unintended linker cleavage, allowing for subsequent release from the solid phase for analysis. The resulting triazoles and their corresponding capture and release yields are shown in Table 13.

TABLE 13

Yields of triazoles 4.25-4.27, 4.31 utilizing solid-phase azide support 4.30, $CuSO_4$, and sodium ascorbate at 1, 3, 6, 9, and 12 hours.

| 1 hr Model Triazole | Alkyne Captured | Triazole in Drain |
|---|---|---|
| 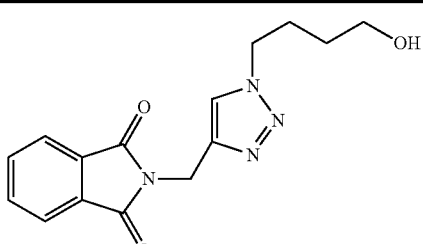<br>4.25 | 89% | 1% |
| 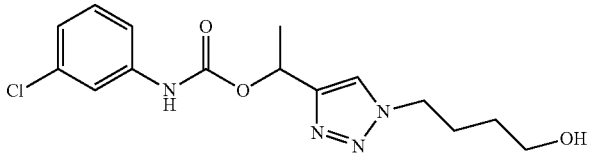<br>4.26 | 70% | 2% |
| 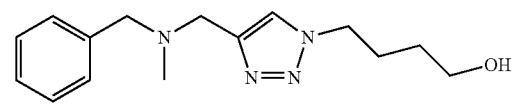<br>4.27 | 68% | 2% |
| 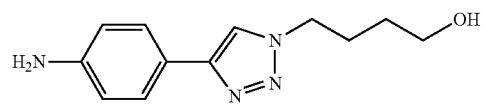<br>4.31 | 78% | 3% |
| Average | 76% | 2% |

| 3 hr Model Triazole | Alkyne Captured | Triazole in Drain |
|---|---|---|
| 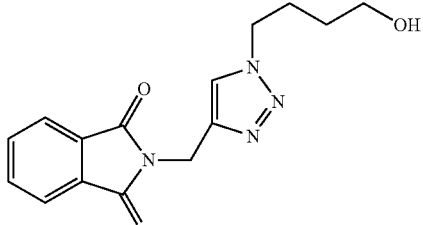<br>4.25 | 99% | 3% |

TABLE 13-continued
| Structure | Alkyne Captured | Triazole in Drain |
|---|---|---|
| 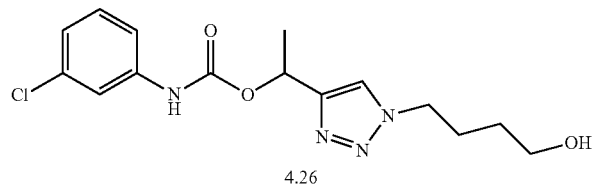 [SMILES: CC(OC(=O)Nc1cccc(Cl)c1)c1cn(CCCCO)nn1] 4.26 | 88% | 0% |
| 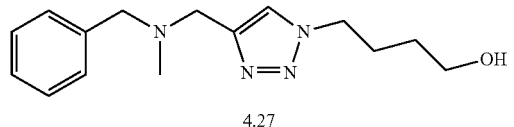 [SMILES: CN(Cc1ccccc1)Cc1cn(CCCCO)nn1] 4.27 | 89% | 2% |
| 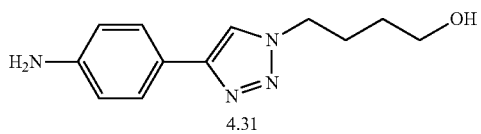 [SMILES: Nc1ccc(-c2cn(CCCCO)nn2)cc1] 4.31 | 96% | 1% |
| Average | 93% | 2% |
| 6 hr Model Triazole | Alkyne Captured | Triazole in Drain |
|---|---|---|
| 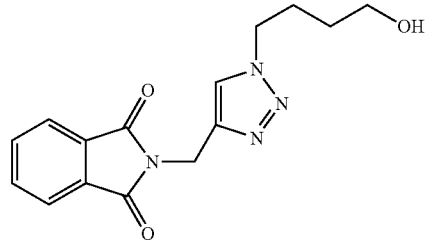 4.25 | 95% | 8% |
| 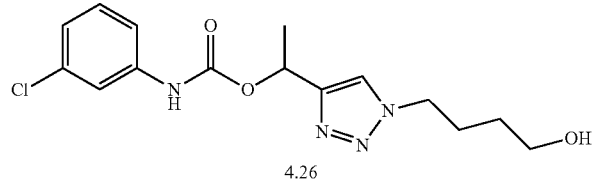 [SMILES: CC(OC(=O)Nc1cccc(Cl)c1)c1cn(CCCCO)nn1] 4.26 | 81% | 5% |
| 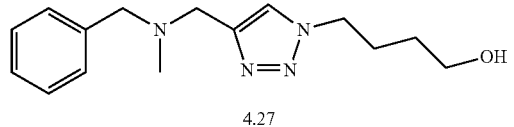 [SMILES: CN(Cc1ccccc1)Cc1cn(CCCCO)nn1] 4.27 | 87% | 11% |
| 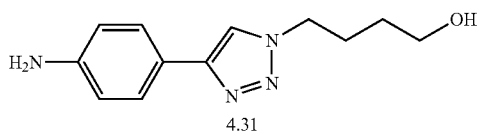 [SMILES: Nc1ccc(-c2cn(CCCCO)nn2)cc1] 4.31 | 90% | 3% |
| Average | 88% | 7% |

TABLE 13-continued
| 9 hr Model Triazole | Alkyne Captured | Triazole in Drain |
|---|---|---|
| 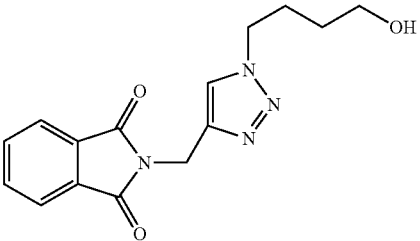<br>4.25 | 95% | 8% |
| 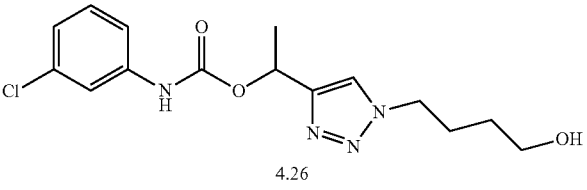 [SMILES: CC(OC(=O)Nc1cccc(Cl)c1)c1cn(CCCCO)nn1]<br>4.26 | 81% | 15% |
| 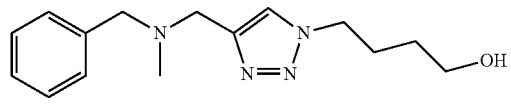<br>4.27 | 87% | 12% |
| 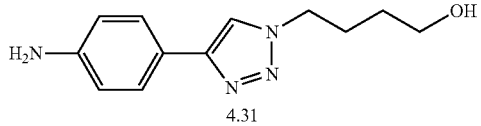 [SMILES: Nc1ccc(-c2cn(CCCCO)nn2)cc1]<br>4.31 | 90% | 3% |
| Average | 88% | 10% |
| 12 hr Model Triazole | Alkyne Captured | Triazole in Drain |
|---|---|---|
| 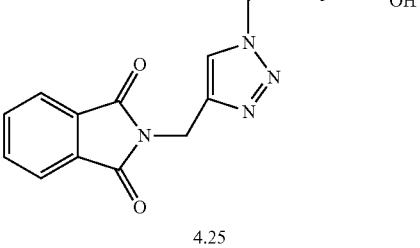<br>4.25 | 92% | 39% |
| 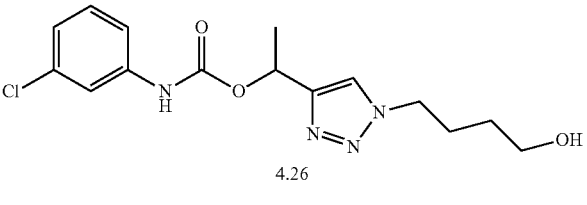 [SMILES: CC(OC(=O)Nc1cccc(Cl)c1)c1cn(CCCCO)nn1]<br>4.26 | 85% | 45% |
| 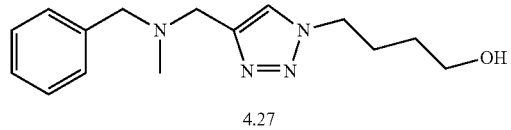 [SMILES: CN(Cc1ccccc1)Cc1cn(CCCCO)nn1]<br>4.27 | 80% | 34% |

TABLE 13-continued

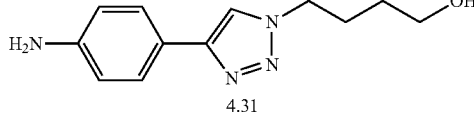

| | | |
|---|---|---|
| 4.31 | 91% | 53% |
| Average | 88% | 7% |

Example 15

Alkyne Capture and Release with Solid-Phase Azide Support 4.30

Using the conditions of Example 14 with a three-hour reaction time, a wider range of alkyne-containing molecules were captured. The molecules are shown in Table 14. To provide quantification using standard curve comparisons, six alkyne standards were transformed into the corresponding triazoles with 4.23 in solution. Previous reaction yields were determined by analyzing the remaining alkyne in the drain with the assumption that all unaccounted for alkyne was converted to the corresponding triazole. The absolute yields are reported in Table 15. Nineteen alkynes were subjected to the coupling procedure. After release with HF.pyridine/pyridine, LC-MS analysis was performed. Seventeen of the alkynes were successfully captured while the other two decomposed during capture. The average enrichment yield was 90% for the six standard alkynes.

TABLE 14

Model Triazoles Generated by Click Chemistry-Based Capture.

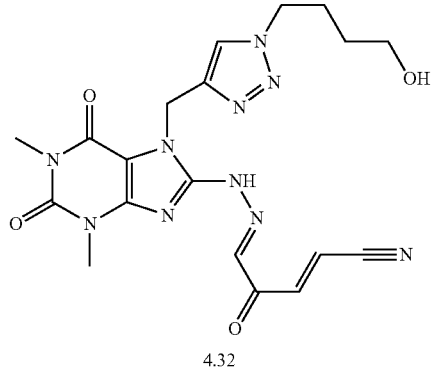 [SMILES: Cn1c(=O)c2c(nc(N/N=C/C(=O)/C=C/C#N)n2Cc2cn(CCCCO)nn2)n(C)c1=O]

TABLE 14-continued
Model Triazoles Generated by Click Chemistry-Based Capture.
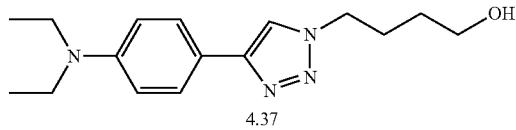 [SMILES: CCN(CC)c1ccc(-c2cn(CCCCO)nn2)cc1]
4.37
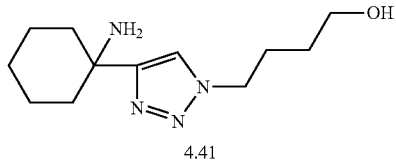 [SMILES: NC1(c2cn(CCCCO)nn2)CCCCC1]
4.41
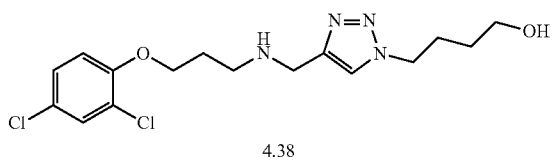 [SMILES: OCCCCn1cc(CNCCCOc2ccc(Cl)cc2Cl)nn1]
4.38
TABLE 15
Yields for the formation of triazoles on solid phase followed by fluoride mediated cleavage of the silyl ether bond.
| Triazole | Conversion and Enrichment Yield |
|---|---|
| 4.25 | 82% |
| 4.26 | 93% |
| 4.21 | 76% |
| 4.42 | 94% |

TABLE 15-continued

Yields for the formation of triazoles on solid phase followed by fluoride mediated cleavage of the silyl ether bond.

| Triazole | Conversion and Enrichment Yield |
|---|---|
| 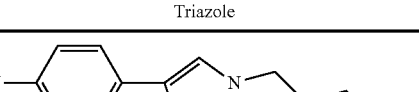<br>4.43 | 98% |
| 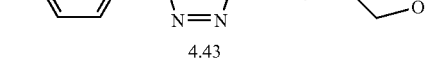<br>4.44 | 99% |

Example 16

Procedure for Alkyne Capture and Release with Solid-Phase Azide Support 4.30

A mixture of 5 alkynes (0.1 eq relative to the resin loading capacity) were dissolved in 400 µL of THF and 100 µL of DMSO. 100 µL of this solution was added to the solid-phase azide support 4.30 (40 mg, 1 eq). Both the $CuSO_4$ (0.01 mmol, 1 eq) and NaAsc (0.02 mmol, 2 eq) were dissolved in 20 µL of phosphate buffered saline (PBS). The copper is added first followed by the NaAsc. The resin mixture was allowed to agitate for 3 hrs at room temperature.

Example 17

Growth of *Streptomyces* strains

Six terrestrial strains of *Streptomyces*, along with *Micromonospora chernisa* were grown on ISP 2 agar plates. The terrestrial strains were purchased from ATCC and revived from a frozen stock with the enclosed instructions. From the spore stock in ISP2, ISP2 agar plates were streaked with each strain and grown at 28° C. for five nights. Each strain was streaked onto 3 plates. Controls plates were also created that contained no bacteria. The strains are listed in Table 16.

TABLE 16

List of bacteria strains and the amount of material obtained after extraction of the agar plate.

| Strain Name | Crude Material from Three Plates (mg) | ATCC Strain Number |
|---|---|---|
| M. chernisa | 157 | 53710 |
| S. cattelya | 210 | 35852 |
| S. cinnamonesis | 81 | 15413 |
| S. coelicolor | 222 | 21666 |
| S. venezuela | 95 | 10712 |
| S. rochei | 200 | 10739 |
| S. avermitilis | 125 | 31267 |

Example 18

Extraction of *Streptomyces* Metabolites

After growth, the plates were placed directly in a −80° C. freezer. After the plates were thoroughly frozen, approximately 2 hrs, the plates were lyophilized to dryness. This dried bacterial sample was cut into small pieces and placed in a flask with a stir bar. Each plate was extracted with 100 mL of n-butanol followed by ethyl acetate. These organic extracts were combined and concentrated to dryness. The extract was subjected to coupling with the conditions described in Example 15, rinsing as described in Example 6, cleavage as described in Example 7, and quantified as described in Examples 8.

Example 19

Synthesis of 5-azidopentyl acetate (4.46)

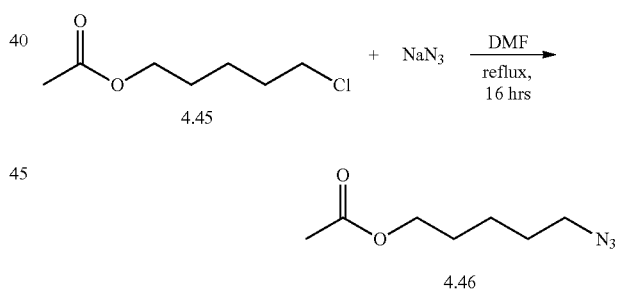

To a 500 mL flask was added 5.0 g (32.8 mmol, 1.0 eq) of 5-chloropentylacetate and dissolved in 100 mL of DMF. Next, 2.6 g (40 mmol, 1.2 eq) of sodium azide was added by a glass pipette. A water condenser was placed onto the flask and the reaction heated to 80° C. for 16 hrs with stirring. The reaction was then cooled to room temperature and quenched with 300 mL of water to dissolve the sodium salts. The aqueous solution was extracted with diethyl ether 3×100 mL. The organic layers were combined and dried with $MgSO_4$. The solution was filtered and concentrated under vacuum with no external heat, resulting in 5-azido-1-pentylacetate (4.46), which was carried onto the next step (described in Example 20) without further purification. $^1$H NMR (500 mHz, DCM): δ: d 4.08 (t, J=6.0 Hz, 2H), 3.33 (t, J=6.2 Hz, 2H), 2.06 (s, 3H), 1.66-1.47 (m, 6H) $^{13}$C NMR (100 MHz, DCM): δ: 171.37, 64.58, 51.89, 29.02, 28.71, 23.73, 21.27

Example 20

Synthesis 4-azido-1-pentanol (4.47)

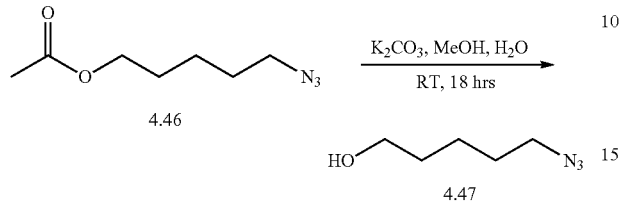

5.1 g of 4-azido-1-pentylacetate (4.46) (33 mmol, 1.0 eq) from Example 19 was dissolved in 30 mL of MeOH and 2 mL of water. This solution was then saturated with $K_2CO_3$ and stirred overnight at room temperature. The reaction was then checked by TLC to confirm conversion of the acetate to the primary hydroxyl. Water (300 mL) was added to dissolve the potassium salt and extracted with diethyl ether 3×100 mL. The organic extracts were combined and dried with $MgSO_4$. The solution was filtered and concentrated under vacuum with no external heat resulting in 4-azido-1-pentanol 4.47: 65% Yield; $^1$H NMR (500 MHz, Acetone-d6): δ: d 3.56 (t, J=4.2 Hz, 2H), 3.45 (t, J=7 Hz, 2H), 1.69-1.37 (m, 6H) $^{13}$C NMR (100 MHz, Acetone): δ: 62.19, 52.01, 33.17, 29.42, 23.90

Example 21

Coupling of 5-Azido-1-Pentanol (4.47) to Resin 4.29 to Provide Solid-Phase Azide Support 4.48

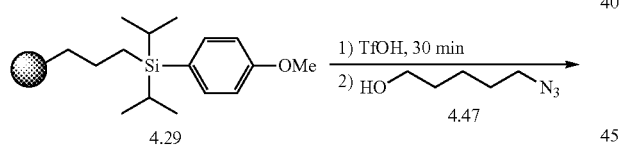

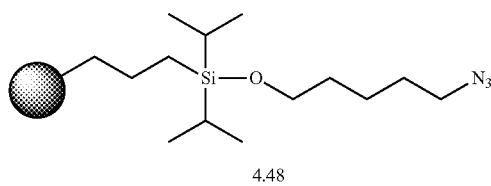

A 10 mL fritted polypropylene column was charged with 200 mg (0.28 mmol) of (4-methoxyphenyl)diisopropylsilypropyl polystyrene (loading capacity of 1.4 mmol/g) resin and equipped with a rubber septum. The resin was flushed with Ar for 10 min and then swollen in 3 mL of anhydrous DCM. Trifluoromethasnesulfonic acid (1.6 mmol, 6 eq) was added to the resin. The resin turned orange and was agitated at room temperature for 30 minutes. After resin activation, the resin was washed with 2 mL anhydrous $CH_2Cl_2$ three times all under Ar. The resin was reswollen in fresh DCM before coupling. With the triflated resin under Ar and swollen, 324 μL (1.1 mmol, 8.0) eq of freshly distilled triethylamine was added to the resin and the color of the resin changed from orange to colorless. 64 mg of 5-azido-1-pentanol 4.47 (0.56 mmol, 2 eq) was added neat to the resin vessel. The vessel was capped and agitated overnight at room temperature. After coupling, the resin was uncapped and rinsed with DCM×3 and THF×3. This resin was used without drying to avoid any degradation. In preparation for subsequent coupling of model alkynes, the resin was aliquoted into 5 eppitubes, each with 500 μL of THF and 40 mg of 4.48.

Example 22

Dual Solid-Phase Azide Resin (4.53

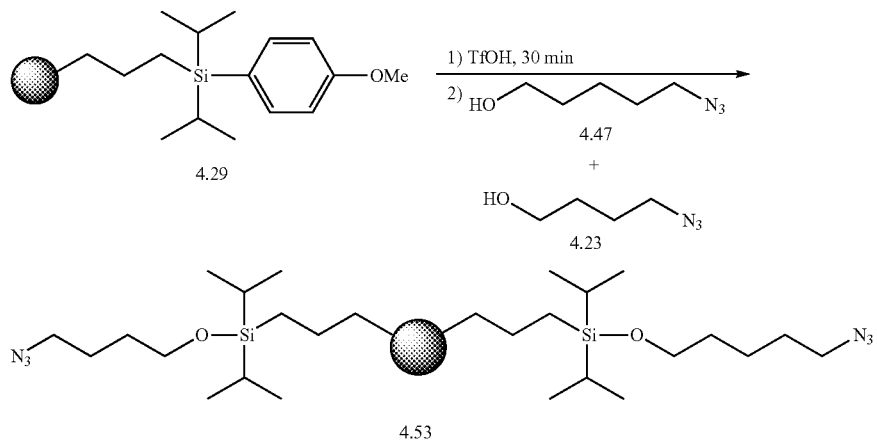

A 10 mL fritted polypropylene column was charged with 200 mg (0.28 mmol) of (4-methoxyphenyl)diisopropylsilypropyl polystyrene (loading capacity of 1.4 mmol/g) resin and equipped with a rubber septum. The resin was flushed with Ar for 10 min and then swollen in 3 mL of anhydrous DCM. Trifluoromethasnesulfonic acid (1.6 mmol, 6 eq) was added to the resin. The resin turned orange and was agitated at room temperature for 30 minutes. After resin activation, the resin was washed with 2 mL anhydrous $CH_2Cl_2$ three times all under Ar. The resin was reswollen in fresh DCM before coupling. With the triflated resin under Ar and swollen, 324 µL (1.1 mmol, 8.0) eq of freshly distilled triethylamine was added to the resin and the color of the resin changed from orange to colorless. 4.47 (0.28 mmol, 1 eq) and 4.23 (0.28 mmil, 1 eq) were added neat to the resin vessel. The vessel was capped and agitated overnight at room temperature. After coupling, the resin was uncapped and rinsed with DCM×3 and THF×3. This resin was used without drying to avoid any degradation. For coupling of model alkynes, the resin was aliquoted into 5 eppitubes, each with 500 µL of THF and 40 mg of 4.53.

Example 23

Dual Solid-Phase Azide Resin Capture of Standard Compounds to Release 4.21, 4.44, 4.51 and 4.52

4.21
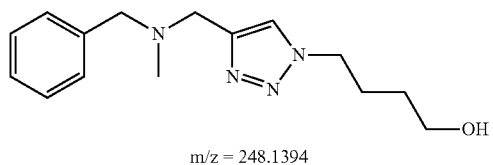
m/z = 248.1394

4.51
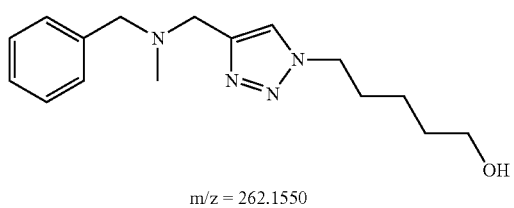
m/z = 262.1550

4.44
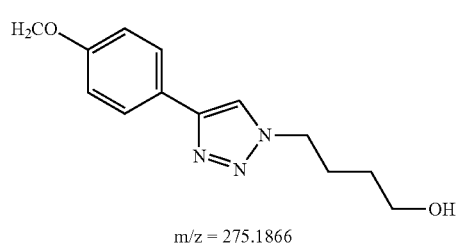
m/z = 275.1866

4.52
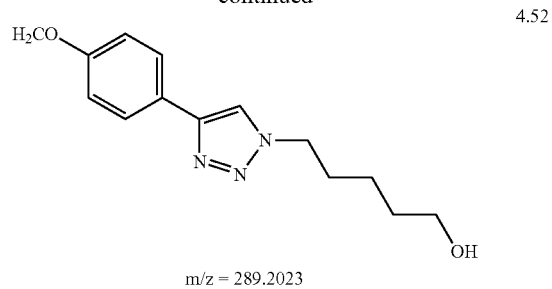
m/z = 289.2023

Using the methods described herein, Dual solid-phase azide resin 4.53 was used to capture standard alkynes which upon release provide a mixture of standard compounds 4.21, 4.44, 4.51 and 4.52.

Example 24

Extracted Ion Chromatograms for Compounds 4.21, 4.44, 4.51, and 4.52

Figure 2:
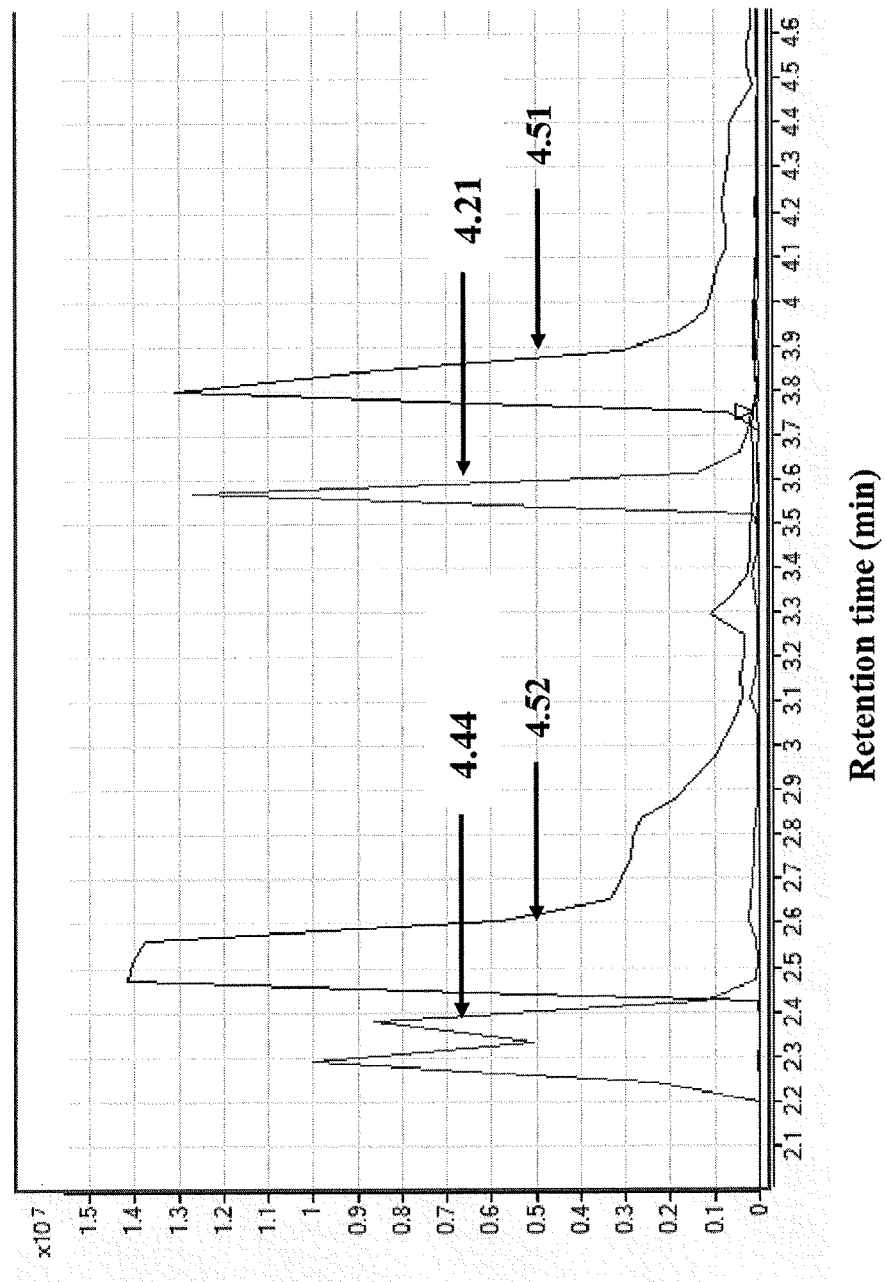
FIG. 2 shows extracted ion chromatograms of compounds 4.21, 4.44, 4.51, and 4.52.

Extracted ion chromatograms were obtained for the released standard compounds 4.21, 4.44, 4.51, and 4.52 of Example 23. Compounds 4.21 and 4.44 each retained a mass of 115 Da for the 4-carbon-based linker resin (4.30) and compounds 4.51 and 4.52 each retained a mass of 129 Da for the 5-carbon-based linker resin (4.48). This 14 Da difference was monitored by LC-ESI-TOF-MS for compounds 4.21, 4.44, 4.51, and 4.52 (Agilent, 6540). The extracted ion chromatograms (shown in FIG. 2) show that elution time effects and the 14 Da difference were due to linker variation are shown in FIG. 2.

Example 25

$MS^2$ of Standard Capture and Release of Compounds 4.21, 4.44, 4.51, 4.52

Fragmentation patterns of standard molecules (4.21, 4.44, 4.51, 4.52) following capture and release were obtained by positive LC-ESI-CID-TOF-MS (Agilent, 6540). It was concluded that the presence of both the 5-carbon and 4-carbon linker and their similar fragmentation spectra would increase confidence in future characterization studies.

Figure 3:
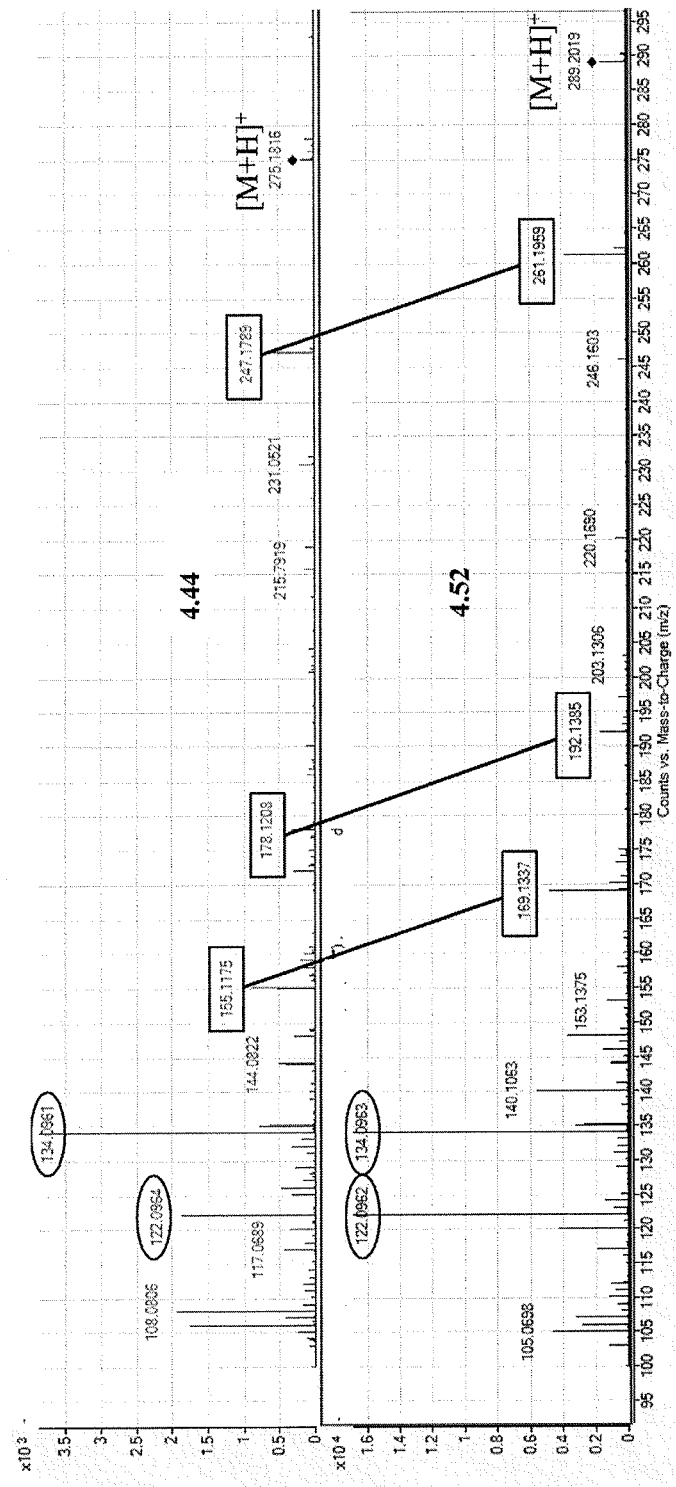
FIG. 3 shows MS$^2$ spectra of a compound with a 4-carbon linker 4.44 (top) and a compound with a 5-carbon linker 4.52 (bottom). Circles indicate identical fragments and boxes represent ions having 14 Da m/z difference due to linker variation.
Figure 4:
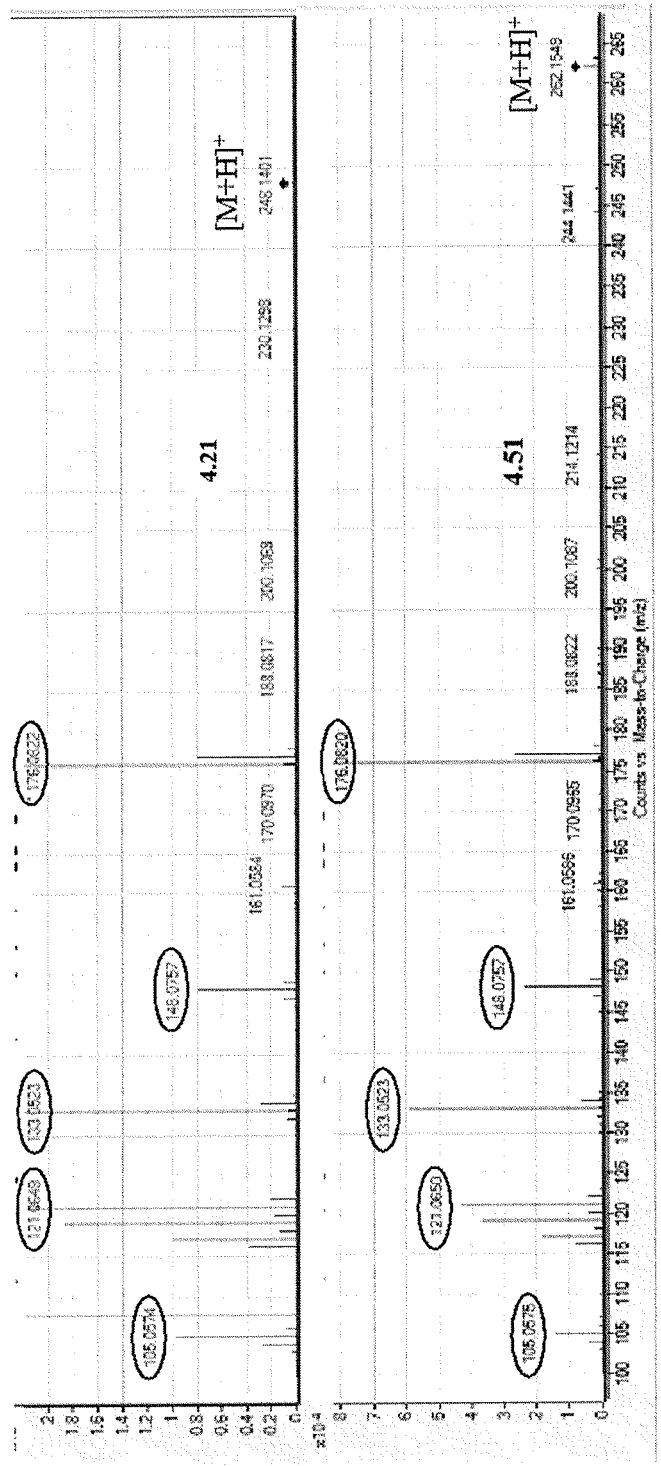
FIG. 4 shows MS$^2$ spectra of a compound with a 4-carbon linker 4.21 (top) and a compound with a 5-carbon linker 4.51 (bottom). Circles indicate identical fragments.

$MS^2$ spectra of a compound with the 4-carbon linker (4.44) and a compound with the 5-carbon linker (4.52) are shown in FIG. 3. Circles indicate identical fragments and boxes represent Δ 14 Da due to linker variation. $MS^2$ of a compound with the 4-carbon linker (4.21) and a compound with the 5-carbon linker (4.51) are shown in FIG. 4. Circles indicate identical fragments.

Example 26

Application of Resins 4.30 and 4.48 to Crude Natural Product Sample

Dual resin 4.53 was applied to natural product samples obtained by growth as detailed in Example 17 from *Streptomyces coelicolor* M145. Crude samples were subjected to UPLC-ESI-CID-TOF-MS (Agilent, 6540) and subject to bioinformatics analysis by GNPS (gnps.ucsd.edu). In a top 3-parent ion experiment, fragmentation profiles were acquired and exported for GNPS analysis. Spectra were scored pairwise by GNPS and prioritized as lead molecules if the following criteria were met: 1) 014 Da spacing between similar spectra (cosine value >0.5) and 2) similar MS² fragmentation profile/neutral loss species for endogenous compound. Following analysis, one lead from *S. coelicolor* M145, [M]=380.16 was prioritized as a putative terminal alkyne containing natural product.

Figure 5:
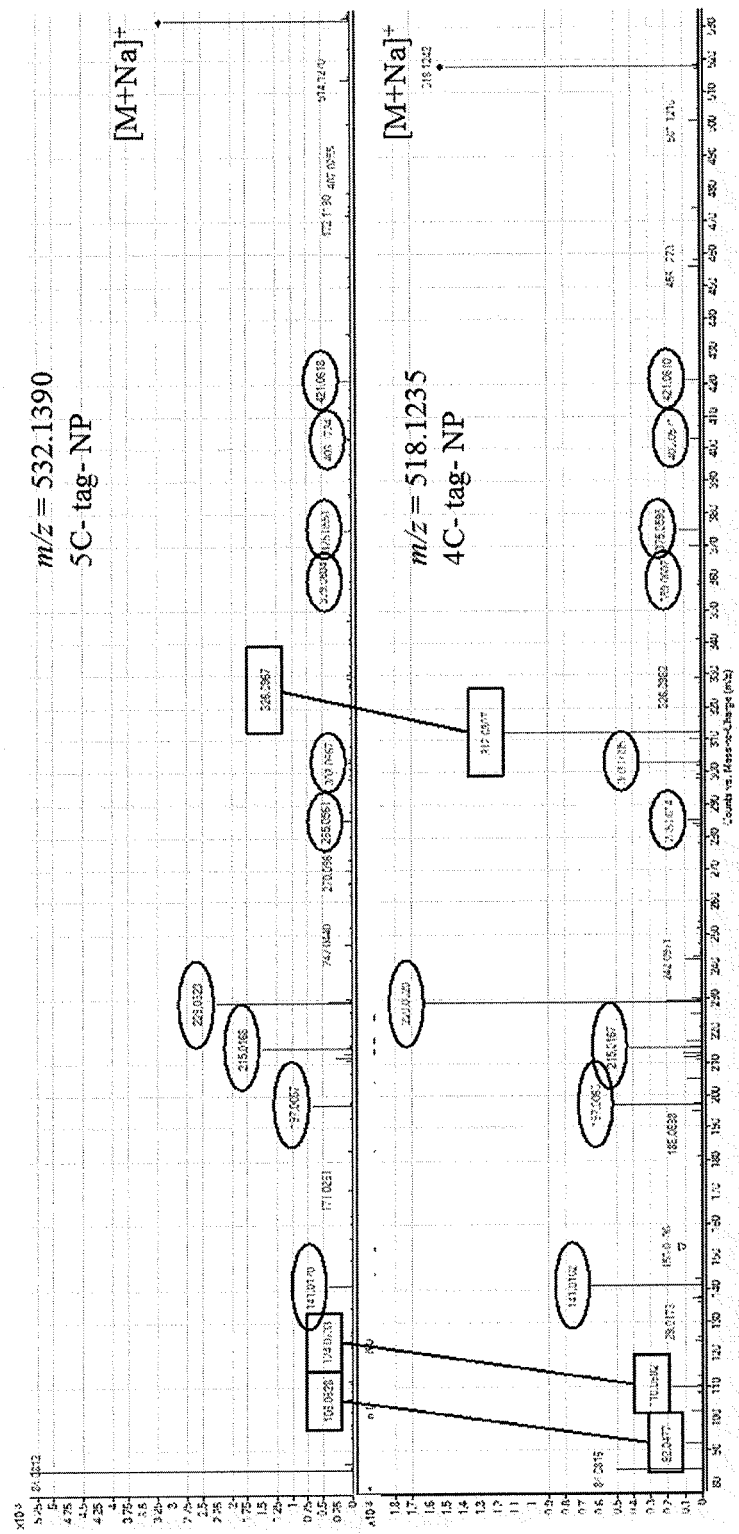
FIG. 5 shows MS$^2$ spectra of putative terminal alkyne containing natural product from *S. coelicolor* M145 with the 5-carbon linker 4.48 (top) and the 4-carbon linker 4.28 (bottom). Circles indicate identical fragments and boxes represent Δ 14 Da due to linker variation and demonstrate the utility of using a two tag strategy for confirmation that the captured species contains an alkyne.

MS² of putative terminal alkyne containing natural product from *S. coelicolor* M145 with the 5-carbon linker (green) and the 4-carbon linker (red) were obtained, as shown in FIG. 5. In FIG. 5, circles indicate identical fragments and boxes represent Δ 14 Da due to linker variation. This example demonstrates the utility of using a two tag strategy for confirmation that the captured species contains an alkyne. The neutral loss of −144 Da (blue, red) and subsequent 74 Da (red) loss were similar to an endogenous, putative compound identified in *S. coelicolor* M145 extract. These data was suggestive of similar structure despite tag addition.

What is claimed is:

1. A functionalized solid support comprising the formula

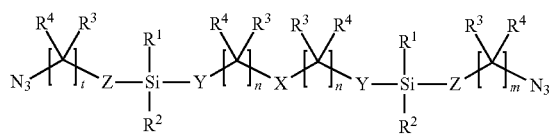

wherein:
X is a solid support;
each Y is independently oxygen or —C(R³)(R⁴)—,
each Z is independently oxygen or —C(R³)(R⁴)—,
R¹ and R² are in each instance independently selected from the group consisting of n-propyl, isopropyl, butyl, isobutyl, sec-butyl, tert-butyl, and optionally substituted aryl;
R³ and R⁴ are in each instance independently selected from the group consisting of hydrogen, methyl, ethyl, n-propyl, isopropyl, butyl, isobutyl, and sec-butyl;
each n is an integer from 0 to 4;
m is an integer from 3 to 6; and
t is an integer from 3 to 6,
wherein m and t are different integers.

2. The functionalized solid support of claim 1, wherein X is a polystyrene bead.

3. The functionalized solid support of claim 2, wherein R¹ and R² are independently selected from the group consisting of phenyl and isopropyl.

4. The functionalized solid support of claim 3, wherein R¹ and R² are isopropyl.

5. The functionalized solid support of claim 4, wherein Y is —CH₂—.

6. The functionalized solid support of claim 4, wherein n is 2.

7. The functionalized solid support of claim 4, wherein Z is oxygen.

8. The functionalized solid support of claim 4, wherein m is 4 and t is 5.

9. The functionalized solid support of claim 1 comprising the formula

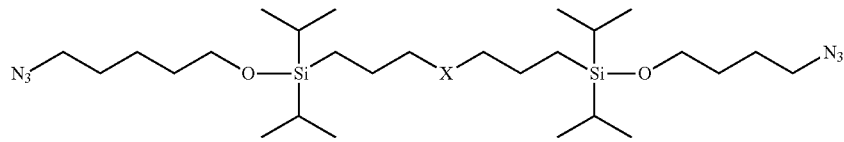

wherein X is a polystyrene bead.

10. A process for isolating an alkyne containing compound, the process comprising the steps of
(a) contacting the alkyne containing compound with the functionalized solid support of claim 1 in the presence of a copper (I) catalyst to provide a bead-supported triazole compound; and
(b) contacting the bead-supported triazole compound with a fluoride source to release a free alcohol.

11. The process of claim 10, wherein the copper (I) catalyst is formed by contacting CuSO₄ with sodium ascorbate.

12. The process of claim 11, wherein sodium ascorbate is added to a mixture of the alkyne containing compound and CuSO₄.

13. The process of claim 10, wherein the fluoride source is HF.

14. The process of claim 10, wherein the contacting step occurs for 1 to 3 hours.

15. The process of claim 10, further comprising washing the bead-supported triazole compound with one or more of tetrahydrofuran, dichloromethane, toluene, dimethylformamide, hexanes, and dimethysulfoxide.

16. The process of claim 10 further comprising washing the bead-supported triazole compound with tetrahydrofuran, dichloromethane, toluene, dimethylformamide, hexanes, and dimethysulfoxide.

17. A process for isolating alkyne containing compound, the process comprising the steps of
(a) contacting the alkyne containing compound with a functionalized solid support comprising the formula

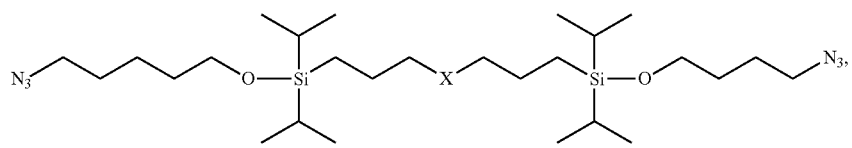

wherein X is a polystyrene bead;

(b) contacting the mixture of step (a) with CuSO₄;
(c) contacting the mixture of step (b) with sodium ascorbate to provide a bead-supported triazole compound;

(d) washing the bead-supported triazole with tetrahydrofuran, dichloromethane, toluene, dimethylformamide, hexanes, and dimethysulfoxide; and
(e) contacting the bead-supported triazole with HF to release a free alcohol.

* * * * *